Figure 1:
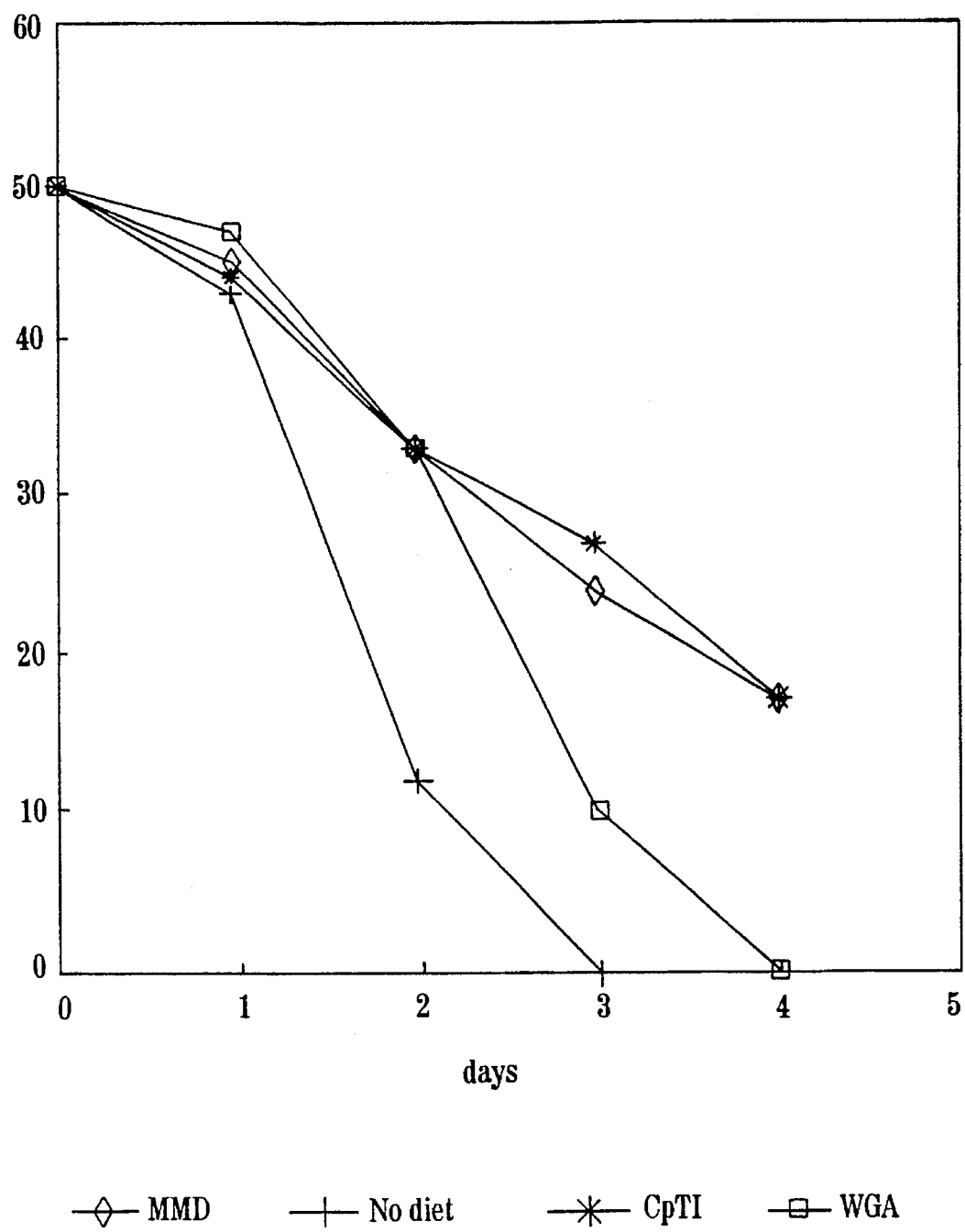

United States Patent [19]
Hilder et al.

[11] Patent Number: 5,604,121
[45] Date of Patent: Feb. 18, 1997

[54] PROTEINS WITH INSECTICIDAL PROPERTIES AGAINST HOMOPTERAN INSECTS AND THEIR USE IN PLANT PROTECTION

[75] Inventors: Vaughan A. Hilder; Angharad M. R. Gatehouse; Kevin Powell, all of Durham; Donald Boulter, Durham City, all of Great Britain

[73] Assignee: Agricultural Genetics Company Limited, Cambridge, Great Britain

[21] Appl. No.: 199,152

[22] PCT Filed: Aug. 26, 1992

[86] PCT No.: PCT/GB92/01565

§ 371 Date: Apr. 21, 1994

§ 102(e) Date: Apr. 21, 1994

[87] PCT Pub. No.: WO93/04177

PCT Pub. Date: Mar. 4, 1993

[30]    Foreign Application Priority Data

Aug. 27, 1991 [GB]  United Kingdom .................... 9118365
Oct. 4, 1991 [GB]  United Kingdom .................... 9121195

[51] Int. Cl.$^6$ ........................ C12N 15/09; C12N 15/29; A01H 1/00; A01H 5/00; C07H 21/04
[52] U.S. Cl. ...................... 435/172.3; 424/405; 424/418; 536/23.6; 536/24.1; 800/205; 935/35; 935/67
[58] Field of Search .................................. 800/200, 205, 800/250, 255, DIG. 57, DIG. 56; 536/23.6, 24.1; 435/172.1, 172.3; 935/35, 67; 424/405, 418

[56]    References Cited

FOREIGN PATENT DOCUMENTS

| | | |
|---|---|---|
| 142924A2 | 9/1984 | European Pat. Off. . |
| 0135343 | 3/1985 | European Pat. Off. . |
| 193259A1 | 1/1986 | European Pat. Off. . |
| 272144A2 | 12/1987 | European Pat. Off. . |
| 289479A2 | 4/1988 | European Pat. Off. . |
| 305275A2 | 8/1988 | European Pat. Off. . |
| 337750A1 | 4/1989 | European Pat. Off. . |
| 339009A2 | 4/1989 | European Pat. Off. . |
| 351924A2 | 7/1989 | European Pat. Off. . |
| 0427529 | 5/1991 | European Pat. Off. . |
| 9109050 | 6/1991 | WIPO . |
| PCT/GB91/ 01290 | 7/1991 | WIPO . |
| 9202139 | 2/1992 | WIPO . |

OTHER PUBLICATIONS

"Lipoxygenase (EC 1.13.11.12), Trypsin Inhibitor and Lectin from Soybeans: Effects on Larval Growth of Manduca Sexta (Lepidoptera: Sphingidae)" by R. H. Shukle et al, Biological Abstracts, vol. 76, 1983, abstract No. 80702. & Environ. Entomol. vol. 12, No. 3, 1983, pp. 787–791.

"Secondary Plant Metabolites as Targets for Genetic Modification of Crop Plants for Pest Resistance", by G. W. Dawson et al., Pesticide Science, vol. 27, 1989, pp. 191–201.

"Gus Fusions: Beta–Glucuronidase s a Sensitive and Versitile Gene Fusion Marker in higher Plants", by R. A. Jefferson et al, EMBO Journal, vol. 6, No. 13, 1987, pp. 3901–3907.

"Histochemical Analysis of CaMV 35S Promoter–Beta–Glucuronidase Gene Expression in Transgenic Rice Plants", by M. J. Battraw et al, Plant Molecular Biology, vol. 15, 1990, pp. 527–538.

"Plant Lipid Peroxidation Manipulation and Effects on Aphid Resistance", by W. Deng et al, Plant Physiology, vol. 99, No. 1, May 1992, p. 109.

Yang et al. 1990, Proc. Natl. Acad. Sci. USA, 87:4144–4148.

*Primary Examiner*—Erich E. Veitenheimer
*Attorney, Agent, or Firm*—Lowe, Price, LeBlanc & Becker

[57]  ABSTRACT

The invention relates to the use for control of Homopteran insect pests of a protein which has toxic or antimetabolic effects on them. According to the invention there is provided a transgenic plant comprising a gene coding for a protein which has toxic or antimetabolic effects on Homopteran insect pests, the gene being associated with a promoter which causes the gene to express the protein in the phloem of the plant.

8 Claims, 12 Drawing Sheets

```
CTCCTTCATT TTCAGTGCAA ATGTGCAATG CTGATTAGAG TTTGCAGATG CTGTTTGGTT      60
TAGTTTAGAT GTGGCATTTT GTTAGTGGTT TCTTTGATGA AAAATTCTTG GCTATGATAA     120
AGTTTGCTTT CTGAATATAT GAATAGTGGC CATGGTTCAA GAAACTCCAG TTAGGTGGGA     180
TAATTTATGG TGATTCTGGG CGCAATTCGG GGAAATTTTT TTTGGCGAGA ATCTTATCAT     240
TGAGATAAAG AGGGCAAGAA TATCAACAGA CTTTTAATCT TAATAAAAAG CACTCTTAGC     300
GTAAGAGCAA AGCATTGCAA TCTCGTGTGA CAAGAACGTT TCTTTTCTC CATCTTTTTC      360
TTTTTTACCA AAAAATGAGT GTTGCCAACT GCTGCACCTT CTTAGGCCGG TTTGTTCTTG     420
TTTGGAACGC ACGGAATGCC CGATGCAAAA AAAAAAAAGA AATGCTGTTA ACAAATCACT     480
GTCCTGACAC GGCTAATTAG GTGGTAATTT GGTGCATCTG CAAAGAAGCA ACAGATGCTT     540
TCTTTCACTG AAAGCATATT TGCATGATTT CTTGTTTCTG CTTGTCCTCT CTCTGATGCT     600
GACTGTATTC CACTCTGCGC TGTAATGCCA TGTTAGTGAT TAATATGTTC AAAAGAGCAT     660
AAAAGAATTG CCAATTGGAT GTTAGAGATT ACTGTGTTGT TCAAAGAGC ATAAAAGAAT      720
TACCAATTTG ATGGTAGATG TTACTAGCAC CACCTTGGTG TTTCCCCATG GTTTTCTGCA     780
ATTCTGCCCA TGATCTTTCT GCTTTTCTGA AAGACCTATG TTTCAGAGGT CAAGCTTCTG     840
GAAGGTTATT AGGAGGGATG AGTCGTCATT TTGTCTGTGG GCCCCACTAG TCAGTGTCAA     900
TAGTTGTAAA GGGTAGAAAT TTTCTTGCTG TTTTTCTTGG AAACAATTTC ATTGCGCCTG     960
ATCTGATGGT CGGTCTGGTA ATCAAATCAC CAGATCCTGA ATCCACCAA ATCAAACCGT     1020
GAGATTTTTG CAGAGGCAAA ACAAGAAAAG CATCTGCTTT ATTTCTCTCT TGCTTTCTTT    1080
TCATCCCCAA CCAGTCCTTT TTTCTTCTGT TTATTTGTAG AAGTCTACCA CCTGCAGTCT    1140
ATTATTCTAC AGAGAAAAG ATTGAAGCTT TTTTTCTCCA AGCTGACAA TGGTGCCGGC      1200
ATATGCTAAT AGGATACTCC CTTCGTCTAG GAAAAAACCA ACCCACTACA ATTTTGAATA    1260
TATATTTATT CAGATTTGTT ATGCTTCCTA CTCCTTCTCA GGTATGGTGA GATATTTCAT    1320
AGTATAATGA ATTTGGACAT ATATTTGTCC AAATTCATCG CATTATGAAA TGTCTCGTTC    1380
GATCTATGTT GTTATATTAT AGACGGAGAT AGTAGATTCG GTTATTTTTG GACAGAGAAA    1440
GTACTCGCCT GTGCTAGTGA CATGATTAGT GACACCATCA GATTAAAAAA ACATATGTTT    1500
TGATTAAAAA AATGGGGAAT TTGGGGGGAG CAATAATTTG GGGTTATCCA TTGCTGTTTC    1560
ATCATGTCAG CTGAAAGGCC CTACCACTAA ACCAATATCT GTACTATTCT ACCACCTATC    1620
AGAATTCAGA GCACTGGGGT TTTGCAACTA TTTATTGGTC CTTCTGGATC TCGGAGAAAC    1680
CCTCCATTCG TTTGCTCGTC TCTGACCACC ATTGGGTATG TTGCTTCCAT TGCCAAACTG    1740
TTCCCTTTTA CCCATAGGCT GATTGATCTT GGCTGTGTGA TTTTTTGCTT GGGTTTTTGA    1800
GCTGATTCAG CGGCGCTTGC AGCCTCTTGA TCGTGGTCTT GGCTCGCCCA TTTCTTGCGA    1860
```

FIGURE 5(a)

```
TTCTTTGGTG GGTCGTCAGC TGAATCTTGC AGGAGTTTTT GCTGACATGT TCTTGGGTTT    1920
ACTGCTTTCG GTAAATCTGA ACCAAGAGGG GGGTTTCTGC TGCAGTTTAG TGGGTTTACT    1980
ATGAGCGGAT TCGGGGTTTC GAGGAAAACC GGCAAAAAAC CTCAAATCCT CGACCTTTAG    2040
TTTTGCTGCC ACGTTGCTCC GCCCCATTGC AGAGTTCTTT TTGCCCCCAA ATTTTTTTTT    2100
ACTTGGTGCA GTAAGAATCG CGCCTCAGTG ATTTTCTCGA CTCGTAGTCC GTTGATACTG    2160
TGTCTTGCTT ATCACTTGTT CTGCTTAATC TTTTTTGCTT CCTGAGGAAT GTCTTGGTGC    2220
CTGTCGGTGG ATGGCGAACC AAAAATGAAG GGTTTTTTTT TTTTGAACTG AGAAAAATCT    2280
TTGGGTTTTT GGTTGGATTC TTTCATGGAG TCGCGACCTT CCGTATTCTT CTCTTTGATC    2340
TCCCCGCTTG CGGATTCATA ATATTCGGAA CTTCATGTTG GCTCTGCTTA ATCTGTAGCC    2400
AAATCTTCAT ATCTCCAGGG ATCTTTCGCT CTGTCCTATC GGATTTAGGA ATTAGGATCT    2460
AACTGGTGCT AATACTAAAG GGTAATTTGG AACCATGCCA TTATAATTTT GCAAAGTTTG    2520
AGATATGCCA TCGGTATCTC AATGATACTT ACTAAAACCC AACAAATCCA TTTGATAAAG    2580
CTGGTTCTTT TATCCCTTTG AAAACATTGT CAGAGTATAT TGGTTCAGGT TGATTTATTT    2640
TGAATCAGTA CTCGCACTCT GCTTCGTAAA CCATAGATGC TTTCAGTTGT GTAGATGAAA    2700
CAGCTGTTTT TAGTTATGTT TTGATCTTCC AATGCTTTTG TGTGATGTTA TTAGTGTTGA    2760
TTTAGCATGG CTTTCCTGTT CAGAGATAGT CTTGCAATGC TTAGTGATGG CTGTTGACTA    2820
ATTATTCTTG TGCAAGTGAG TGGTTTTGGT ACGTGTTGCT AAGTGTAACC TTTCTTTGCA    2880
GTTCCTGAAA TTGAGTCATG GCTGCCAAGC TAGC                                 2914
```

FIGURE 5(b)

PROTEINS WITH INSECTICIDAL PROPERTIES AGAINST HOMOPTERAN INSECTS AND THEIR USE IN PLANT PROTECTION

This invention relates to the use of proteins to control sap-sucking insects belonging to the Order Homoptera which are harmful to plants, and methods for using them to introduce enhanced resistance to Homopteran pests into plants.

BACKGROUND OF THE INVENTION

The order Homoptera, often regarded as a separate sub-order of the order Hemiptera, includes those insects known as plant bugs. These insects have piercing and sucking mouth-parts and feed upon sap. They include the aphids [family Aphididae], white flies [Aleyrodidae], planthoppers [Delphacidae], leafhoppers [Cicadellidae], jumping plant lice [Psyllidae] woolly aphids [Pemphigidae], mealy bugs [Pseudococcidae], and scales [Coccidae, Diaspididae, Asterolecaniidae and Margarodidae]. Many species are serious pests of agricultural and horticultural crops and of ornamental plants, including, for example, pea aphid, black bean aphid, cotton aphid, green apple aphid, glasshouse-potato aphid, leaf-curling plum aphid, banana aphid, cabbage aphid, turnip aphid, peach-potato aphid, corn leaf aphid, wheat aphid, brassica whitefly, tobacco whitefly, glasshouse whitefly, citrus blackfly, small brown planthopper, rice brown planthopper, sugarcane planthopper, white-backed planthopper, green rice leafhopper, beet leafhopper, cotton jassid, zig-zag winged rice leafhopper, apple sucker, pear sucker, woolly apple aphid, lettuce root woolly aphid, grape phylloxera, long-tailed mealybug, pineapple mealybug, striped mealybug, pink sugarcane mealybug, cottony cushion scale, olive scale, mussel scale, San Jose scale, California red scale, Florida red scale and coconut scale.

Crop damage as a result of feeding by these insects occurs in a number of ways. Extraction of sap deprives the plant of nutrients and water leading to loss of vigour and wilting. Phytotoxic substances present in the saliva of some species, and mechanical blockage of the phloem by feeding may result in distortion and necrosis of foliage [as in 'hopperburn'] and in blindness or shrunken kernels in grain crops. Injury, caused by insertion of the mouthparts leaves lesions through which plant pathogens may enter. Production of copious 'honeydew' may allow sooty moulds to develop or its stickiness may interfere with the harvesting of cereals and cotton. Some of the most serious damage caused by these pests is indirect, due to their role as vectors of plant viruses. Examples of serious virus diseases spread by Homopterans include maize streak, beet curly-top, northern cereal mosaic, oat rosette, pear decline, tobacco mosaic, cauliflower mosaic, turnip mosaic, rice orange leaf, rice dwarf, rice yellow dwarf, rice transitory yellowing, rice grassy stunt, sugarcane Fiji disease, cassava mosaic, cotton leaf-curl, tobacco leaf-curl, sweet potato virus B, groundnut rosette, banana bunchy top, citrus tristeza, pineapple mealybug wilt and cocoa swollen shoot. Reduction in the Homopteran insect populations would be useful in limiting the spread of these and other viral diseases in crops. This invention addresses the problem of control of these sucking insect pests.

Since the late 1940s, methods to control these pests have centred on the exogenous application of synthetic organochemicals. Because of their feeding habits, effective insecticides must act on contact or be systemic within the plant. Insecticides of the chlorinated hydrocarbon, substituted phenol, organophosphate, carbamate and pyrethrin classes have been used, but this method of plant protection is encountering increasing problems known to those versed in the art. The problem of the development of pest insect resistance to pesticides is particularly acute amongst Homopterans, where the typically short generation time allows the emergence of resistant biotypes very rapidly. For example, the brown planthopper of rice can apparently develop a new biotype in only about 18 months.

Biological control of pest insects has been favoured as an alternative strategy. Such an approach exploits the natural viral, bacterial or fungal pathogens or the natural invertebrate or vertebrate predators of the target pest to limit its population. Examples include granulosis and polyhedrosis viruses effective against specific caterpillar and sawfly larvae [eg. Heliothis PHV] and *Bacillus thuringiensis kurstaki*, effective against certain caterpillars. Pathogenic/parasitic fungi have been identified in a wide range of insect classes, including Homopterans; *Venicilium lecanii* has proved useful in the control of aphids and whitefly in glasshouses, though not in the field. Free living and parasitic predators of pests have been used with some success, particularly in stable ecosystems such as glasshouses and orchards, for example various Hymenopteran, Coleopteran and Acarinan insects have been used for the control of aphids and whitefly in glasshouses. The widespread introduction of biological control measures has, however, been limited by problems of large scale production, widespread application and lack of persistence of the control agents in the field.

A preferred solution is to use inherently insect resistant cultivars, varieties or lines as part of an integrated pest management programme. Production of such resistant lines, which may exhibit pest avoidance, non-preference, antibiosis or pest tolerance, is a major goal of many conventional plant breeding programmes for crop improvement. In those cases where a biochemical mechanism of resistance to Homopterans has been determined, it resides in altered levels of specific, non-protein secondary plant metabolites. This approach is limited by the extent of genetic variability for resistance which is available within the interbreeding germplasm. Often a source of resistance to a specific pest is not available. It is further limited by the long time scale required to produce a resistant cultivar imposed by the large number of backcrosses necessary to introgress the character into an agronomically acceptable genetic background. In response to the introduction of new insect resistant lines of plants, new insect biotypes arise to which the plants are not resistant. As with synthetic insecticides, development of resistance breaking biotypes is a particular problem with Homopterans. For example, many rice varieties resistant to the brown planthopper [BPH] have been developed at the International Rice Research Institute, Manila, Philippines [IRRI] which have given excellent control of this bug in the field for a time. However, resistance breaking biotypes have developed in some localities to the extent that local rice production is threatened. As fast as new BPH resistant varieties come out of the IRRI programme, new resistance breaking biotypes of the insect evolve. There is thus a continuous need for novel sources of BPH resistance genes to incorporate into the breeding programme.

Genetic engineering may make a useful contribution here since it allows genes encoding insecticidal proteins to be inserted into elite lines of crop plants in a single step irrespective of the natural source of the protein or its ability to cross-breed with the host. A number of cases are known to the art wherein a foreign gene is introduced into a transgenic plant which specifies the production of levels of protein which are toxic or antimetabolic to insects which feed on the plant by chewing the leaves, roots, stems or fruits.

European Patent Application 0142 924 [Agrigenetics Research Associates Ltd.] describes the production in transgenic plants of a *B. thuringiensis* delta endotoxin which is larvicidal to certain Lepidoptera. Similarly, EPA 0193 259 [Plant Genetic Systems NV] describes production of a Lepidopteran-toxic protein in transgenic plants expressing a truncated Bt toxin gene. Bt toxin genes useful for controlling Coleopteran insects on introduction into transgenic plants are described in EPA 0289 479 [Monsanto Co.] and EPA 0305 275 [Plant Genetic Systems NV]. EPA 0339 009 [Monsanto Co] describes the potentiation of effectiveness of a Lepidopteran specific Bt toxin by co-expressing trypsin inhibitor in transgenic plants.

EPA 0272 144 [Agricultural Genetics Co.] teaches that the expression of a gene encoding trypsin inhibitor from cowpeas in transgenic plants enhances resistance to both Lepidopteran and Coleopteran pests.

EPA 0337 750 [Plant Cell Research Institute Inc.] describes the introduction and expression of genes encoding arcelin, a storage protein of wild Phaseolus bean seeds, in transgenic plants and suggests that it might be useful in protection from Coleopteran pests.

EPA 0351 924 [Shell International Research Maatschappij BV] describes the introduction and expression of genes encoding the lectin from the garden pea in transgenic plants enhancing resistance to Lepidopteran larvae. PCT/GB91/01290 [Agricultural Genetics Co.] relates to the use of genes encoding lectins from the monocotyledonous Families Amaryllidaceae and Alliaceae for control of Lepidopterans and Coleopterans, without associated mammalian toxicity. EPA 0427 529 [Pioneer Hi-Bred International Inc.] describes the use of a variety of lectins to control Lepidopteran and Coleopteran pests.

Each of these proteins have to be ingested to exert their insecticidal effect, and their primary site of action appears to be the midgut [Hoffmann, C. et al. {19882} *Proc. Natl. Acad. Sci.* USA 85, 7844-; Gatehouse A. M. R. and Boulter, D. {1983} *J. Sci. Food Agric.* 34, 345–350; Gatehouse et al. {1984} *J. Sci. Food Agric.* 35, 373–380]. However, the digestive system in sap-sucking Homopterans is unusual amongst the Insecta in a number of important respects, for example they lack a crop, the midgut is not lined by a peritrophic membrane and hydrolytic digestive enzymes are absent [see eg. Terra, W. R. {1990} *Annu. Rev. Entomol.* 35, 181–200]. In view of the radically different mode of feeding, nature of food and necessary organisation of the gut between plant tissue chewing insects and sap-sucking insects, it would be very surprising if proteins which had insecticidal activity against one class of insects were to be effective against the other.

BRIEF DESCRIPTION OF THE DRAWINGS

FIG. 1 illustrates artificial diet bioassay data with the brown planthopper to distinguish between effective [eg. wheatgerm agglutinin] and non-effective [eg. cowpea trypsin inhibitor] for controlling Homopteran insect pests.

FIG. 2 illustrates artificial diet bioassay data with *Myzus persicae,* the peach potato aphid, showing the reduction in insect survival in the presence of GNA, the snowdrop lectin.

FIGS. 3(*a*)–3(*c*) illustrate the gene map of plasmid pSC which contains a promoter useful for the phloem specific expression of foreign genes in transgenic plants, and of intermediate plasmids pDB2 and pDA used in its production.

FIG. 4 illustrates the gene map of plasmid pSS24NN30B, which is a useful intermediate plasmid containing the RSs1 gene promoter/intron 1 sequences.

FIGS. 5(*a*)–5(*b*) (SEQ ID NO: 4) illustrate the nucleotide sequence of the+strand of the RSs1 promoter +intron 1 region of the insert in plasmid pSS24NN30B; a useful sequence for the phloem specific expression of genes in plants from a monocotyledenous promoter.

FIGS. 6(*a*)–6(*b*) illustrate the gene map of plasmid pSCB, which is useful as a phloem specific expression cassette, and of plasmid pSC1GNA which is a specific expression vector for the snowdrop lectin structural gene.

FIG. 7 illustrates the gene map of plasmid pBRSSLT2, which is useful as a binary vector for the expression of GNA from the RSs1 gene promoter in the phloem of transgenic plants.

FIGS. 8(*a*)–8(*c*) illustrate the gene map of plasmid pSCGNAR1 which is a phloem specific expression construct for the snowdrop lectin gene for introduction into plants by direct DNA uptake. Also illustrated is the gene map of pSCGNAR2, a similar plasmid but which allows selection for hygromycin resistance, and of pJITAph, an intermediate in the construction of pSCGNAR2.

FIG. 9 illustrates the gene map of plasmid pRSSLTR, which is useful for expression of GNA from the RSs1 promoter in the phloem of transgenic rice plants.

FIG. 10 illustrates data from whole plant bioassays of GNA-expressing transgenic and control tobacco plants against *Myzus persicae,* the peach potato aphid.

FIG. 11 illustrates data from leaf disc bioassays of GNA-expressing transgenic and control tobacco plants against *M. persicae.*

DISCLOSURE OF THE INVENTION

It has now been demonstrated that certain proteins have potent insecticidal activity when administered enterally to rice brown planthopper [BPH]. Thus, this invention provides a method of killing Homopteran insects, including BPH, by administering enterally to the insects an insecticidal amount of a protein such as *Galanthus nivalis* lectin [snowdrop lectin; GNA] and *Triticum vulgare* lectin [wheatgerm agglutinin; WGA]. The target insects feed exclusively upon phloem sap so the protein must be presented to them in the sap. Externally applied proteins are not mobilised into the phloem sap of treated plants. However, the genes which encode these proteins can be isolated, cloned, inserted into an appropriate expression cassette and introduced into the genome of a susceptible plant such that expression in the phloem occurs. Thus the preferred embodiment of the method involves inserting into the genome of the host plant a DNA sequence encoding a Homopteran killing protein such as snowdrop lectin or wheatgerm agglutinin in the correct orientation with respect to phloem specific promoter sequences which are active in the plant.

The most commonly employed promoter sequences for gene expression in plants are not particularly appropriate for the purposes of this invention. Promoter sequences such as those derived from the cauliflower mosaic virus [CaMV] 35S gene [Odell, J. T. et al. {1985} *Nature* 313, 810–812], Agrobacterium nopaline synthase [nos] and octopine synthase [ocs], small-subunit ribulose-1,5-bisphosphate carboxylase gene from soyabean [Berry-Lowe et al. {1982} *J. Molec. Appl Genet.* 1, 483–498], chlorophyll a–b binding protein gene [Simpson et al. {1986} *Nature* 323, 551–554] have been favoured for expression of proteins with insecticidal activity to chewing insects of the orders Lepidoptera and Coleoptera. These, however, do not have the required specificity for the preferred embodiments of the present invention. It has now been demonstrated that the 4×B2+A promoter construct [Benfey et al. {1990} *EMBO J.* 9, 1677–1684], the oilseed rape extensin gene promoter [Shirsat A. et al. {1991} *Plato Molec. Biol.* 17, 701–709] and the rice sucrose synthetase gene promoter [Yang, N-S. and Russell, D. {1990} *Proc. Natl. Acad. Sci.* USA 87, 4144–4148] direct high levels of expression in the phloem tissue of transgenic plants. Thus, the preferred embodiment of this invention involves chimaeric DNA constructs wherein the sequences encoding a Homopteran-killing protein are placed under the control of a sequences selected from the 4×B2+A promoter, the extensin gene promoter or the rice sucrose synthetase gene promoter. These constructs also include a polyadenylation signal and transcription termination signal in the correct orientation. These sequences are provided by the nopaline synthase gene [NOS] terminator region.

These gene expression constructs are linked to additional structural genes which direct expression of a selectable marker gene to facilitate selection of transformed plant cells. Preferred selection agents are the antibiotics kanamycin and hygromycin, although many alternatives will be known to those skilled in the art.

These expression constructs may be maintained and propagated in many of the plasmid vectors/bacterial hosts known to the art.

The plant is preferably a crop plant susceptible to infestation and damage by Homopteran insects. Preferred plants to be transformed according to the methods of this invention include rice, maize, wheat, barley, sorghum, oats, millet, apple, pear, citrus, sugar beet, potato, tomato, tobacco, cotton etc.

The following description further exemplifies the compositions of this invention and the methods of making and using them. However, it will be understood that alternative methods, known to those of ordinary skill in the art, can also be employed. Many standard methods of molecular biology are well known in the art and are not detailed here, being well documented in, for example, Sambrook, J. et al. [1989: *Molecular Cloning: A Laboratory, Manual.* 2nd edition. Cold Spring Harbour Press. N.Y.].

EXAMPLE 1

Identification of Homopteran killing proteins

There are no a priori grounds for expecting insecticidal activity in any protein against Homopterans, but having made the surprising observation that GNA displayed such activity the susceptibility of an Homopteran to a variety of proteins administered in an artificial diet was evaluated. Rice brown planthopper [BPH] *Nilaparvata lugens* was used initially to screen a number of proteins for insecticidal activity.

1.1. Maintenance of insects

Insects were reared under growth room conditions of 16h daylight, 25±2° C. temperature and 75–85% relative humidity. The insects were maintained on 40–60 day old *Oryza sativa* plants of the susceptible variety 'Taichung Native 1' [TN1] and new plants were introduced weekly into the rearing cages in order to maintain a stock culture.

1.2. Artificial diet

The artificial diet used, referred to as MMD 1, was based on that of Mitsuhashi [1974: *Rev. Plant Protec. Res.* 7, 57–67] which is in turn a modification of the Mittler and Dadd [1962: *Nature* 195, 404] diet for aphids. The ingredients are listed in Table 1. The diet is rich in nutrients and to avoid microorganism contamination was dispensed into 10 ml aliquots through a Millipore™ filter of 0.2 μm pore size. The diet was stored at −20° C., to avoid deterioration of the unstable ingredient sodium ascorbate, and kept in plastic containers. Diets were stored at −20° C. for a maximum of 4 weeks.

TABLE 1

| Composition of MMD1 diet | |
|---|---|
| Ingredient | mg/100 ml |
| $MgSO_4.7H_2O$ | 123 |
| $K_2HPO_4$ | 750 |
| Sucrose | 5000 |
| L-alanine | 100 |
| L-arginine HCl | 270 |
| L-asparagine | 550 |
| L-aspartic acid | 140 |
| L-cysteine | 40 |
| L-glutamic acid | 140 |
| L-glutamine | 150 |
| Glycine | 80 |
| L-histidine | 80 |
| L-isoleucine | 80 |
| L-leucine | 80 |
| L-lysine HCl | 120 |
| L-methionine | 80 |
| L-phenylalanine | 40 |
| L-proline | 80 |
| DL-serine | 80 |
| L-threonine | 140 |
| L-tryptophan | 80 |
| L-tyrosine | 40 |
| L-valine | 80 |
| Thiamine HCl | 2.5 |
| Riboflavin | 0.5 |
| Nicotinic acid | 10 |
| Pyridoxine HCl | 2.5 |
| Folic acid | 0.5 |
| Calcium pantothenate | 5 |
| Inositol | 50 |
| Choline chloride | 50 |
| Biotin | 0.1 |
| Sodium ascorbate | 100 |
| $FeCl_3.6H_2O$ | 2.23 |
| $CuCl_2.2H_2O$ | 0.27 |
| $MnCl_2.4H_2O$ | 0.79 |
| $ZnCl_2$ | 1.19 |
| $CaCl_2.2H_2O$ | 3.12 |

Tyrosine was first dissolved in 1N HCl as it is not readily soluble in distilled water. Riboflavin was heated in a small volume of water to assist with its dissolution. Where necessary the diet was adjusted to pH6.5 with KOH and HCl.

The diet solution was incorporated in a feeding vessel based on a modification of that described by Mitsuhashi [1974] for the rearing of planthoppers and leafhoppers. This consisted of a circular plastic container, 35 mm diameter, 10 mm depth, with one end open. The base of the container was lined with a 35 mm diameter disc of Whatman™ No1 filter paper previously soaked in distilled water. The open end of the vessel was covered with a piece of Parafilm™ membrane, stretched to 4 times its original area. A 200 µl droplet of the diet solution was placed on this basal membrane and covered with a further layer of stretched Parafilm membrane to provide a feeding sachet.

1.3. Feeding trials

Nymphs of *N. lugens* were removed from the host plant by gently tapping the stem and 5 nymphs were transferred to each bioassay vessel using a fine paintbrush. Both newly emerged first instar or third instar larvae have been used; survival is better on control diets of the latter, more robust larvae. Test proteins were incorporated in the artificial diet at 0.1% [w/v]. A control of diet without added protein and another of no diet at all was included in each series of tests. Ten replicates of each treatment were performed. The vessels were maintained in a cooled incubator at 16h daylight, 25±2° C. Diets were changed daily to ensure a fresh nutrient supply. The number of nymphs surviving was recorded daily.

Results

This diet does not support the development of the nymphs to adulthood, but survival of up to 18 days are achieved on MMD1, by which time the nymphs have reached the 4th instar. Survival to adulthood can be achieved by putting the feeding sachet under pressure [by modifying the feeding chamber to incorporate a ca. 5 cm head of water over the sachet], but is not necessary to demonstrate insecticidal effects of proteins. Some insects survive for 2 days in the absence of diet [FIG. 1]. The increase in mortality, corrected according to Abbott [1925: *Journal of Economic Entomology*, 18, 265–267] on the day when all 'no diet' insects were dead was used as the measure of effectiveness of the test protein. It will be noted that this formula produces a negative value for corrected mortality if insect survival is enhanced in the presence of the test protein compared to controls. A number of proteins were found which showed such a beneficial [to the insects] effect. Survival frequencies were subjected to statistical analysis by a G-test of independence [eg. Sokal, R. R. & Rohlf, F. J. Introduction to biostatistics. W. H. Freeman and Co., San Francisco (1973) pp.286–303]. Yates' correction was applied to the data where appropriate [ie. n<200]. As may be judged from FIG. 1, an increase in mortality of >50% at this time indicates substantial toxic or antimetabolic effect. The results for 1st instar nymphs are shown in Table 2 and for 3rd instar in Table 3.

TABLE 2

Bioassay of various proteins for anti-insect activity against 1st instar *N. lugens*

| PROTEIN | CORRECTED MORTALITY | $G_{adj}$ | $P_{[HO:CON=EXP]}$ | Significance |
|---|---|---|---|---|
| Inert proteins | | | | |
| BSA | −138 | 12.554 | <0.001 | *** |
| OVA | 4 | 0 | >0.05 | N.S |
| Lectins | | | | |
| GNA | 76 | 42.224 | <0.001 | *** |
| PHA | 27 | 4.528 | <0.05 | * |
| PLA | −2 | 0 | >0.05 | N.S |
| WGA | 75 | 42.840 | <0.001 | *** |
| LCA | N.D | | | |
| HGA | N.D | | | |
| JCA | N.D | | | |
| ConA | N.D | | | |
| PPL | N.D | | | |
| Enzyme inhibitors | | | | |
| CpTI | −13 | 0.160 | >0.05 | N.S |
| WAX | N.D | | | |
| Enzymes | | | | |
| Chase | N.D | | | |
| LPO | N.D | | | |
| PPO | N.D | | | |

OVA - ovalbumin; BSA - bovine serum albumin; GNA - snowdrop lectin; PHA - phytohaemagglutinin; PLA - pea lectin A; WGA - wheatgerm agglutinin; LCA - lentil lectin; HGA - horse gram lectin; JCA - jacalin lectin; ConA - concanavalin A; PPL - potato lectin; CpTI - cowpea trypsin inhibitor; WAX - wheat insect- specific α-amylase inhibitor; Chase - bean endochitinase; LPO - soyabean lipoxidase: PPO - Streptomyces polyphenol oxidase. N.D - not determined.

TABLE 3

Bioassay of various proteins for anti-insect activity against 3rd instar *N. lugens*

| PROTEIN | CORRECTED MORTALITY | $G_{adj}$ | $P_{[HO:CON=EXP]}$ | Significance |
|---|---|---|---|---|
| Inert proteins | | | | |
| BSA | N.D | | | |
| OVA | N.D | | | |
| Lectins | | | | |
| GNA | 79 | 104.642 | <0.001 | *** |
| PHA | −145 | 9.752 | <0.005 | ** |
| PLA | N.D | | | |
| WGA | 78 | 61.724 | <0.001 | *** |
| LCA | 22 | 4.336 | <0.05 | * |
| HGA | 28 | 2.726 | >0.05 | N.S |
| JCA | −3 | 0 | >0.05 | N.S |
| ConA | 30 | 1.980 | >0.05 | N.S |
| PPL | −10 | 0.164 | >0.05 | N.S |
| Enzyme inhibitors | | | | |
| CpTI | N.D | | | |
| WAX | −4 | 0 | >0.05 | N.S |
| Enzymes | | | | |
| Chase | −55 | 9.762 | <0.005 | ** |
| LPO | 85 | 63.724 | <0.001 | *** |
| PPO | 12 | 0.330 | >0.05 | N.S |

Abbreviations as in Table 2.

The lectins from snowdrop [*Galanthus nivalis*, GNA] and wheatgerm [*Triticum vulgare*, WGA] have substantial insecticidal activity against the brown planthopper and are useful in protecting plants against Homopteran insects. The enzyme lipoxidase [lipoxygenase; linoleate: oxygen oxidoreductase; EC 1.13.11.12] also has substantial insecticidal activity.

1.4. Feeding trials against green leafhoppers

It has now been found that certain proteins which are effectively insecticidal in artificial diet bioassays against brown planthoppers are also effective against sap-sucking insects which belong to a quite different taxonomic Family, the Cicadellidae [=Jassidae], within the Order Homoptera.

The green leafhopper, *Nephotettix nigropictus,* is a sporadically serious pest of rice and the vector for a number of disease causing viruses including rice yellow dwarf and transitory yellowing. Green leafhoppers were maintained and bioassayed as described above [1.1–1.3]. The results, presented in Table 4, show that snowdrop lectin is effectively insecticidal against the leafhopper as well as the brown planthopper.

TABLE 4

Bioassay of various proteins for anti-insect activity against 3rd instar *Nephotettix nigropictus* [green leafhopper].

| PROTEIN | CORRECTED MORTALITY | $G_{adj}$ | $p_{[HO:CON=EXP]}$ | Significance |
|---|---|---|---|---|
| Lectins | | | | |
| GNA | 87 | 11.110 | <0.001 | *** |
| WGA | 15 | 0.674 | >0.05 | N.S |
| Enzymes | | | | |
| LPO | 5 | 0.052 | >0.05 | N.S |

Abbreviations as in Table 2.

1.5. Feeding trials against peach potato aphids

It has further been found that snowdrop lectin is effectively insecticidal in artificial diet bioassays not only against brown planthoppers and green leafhoppers but also against sap-sucking insects which belong to yet another quite different taxonomic Family, the Aphididae, within the Order Homoptera. The Aphididae are the most important group of plant bugs and are better adapted for life in the temperate zones than the tropics. *Myzus persicae,* the peach potato or green peach aphid, is a serious, polyphagous pest worldwide, and acts as the vector for over 100 different disease causing viruses. Many biotypes show multiple resistance to conventional chemical pesticides.

Figure 2:
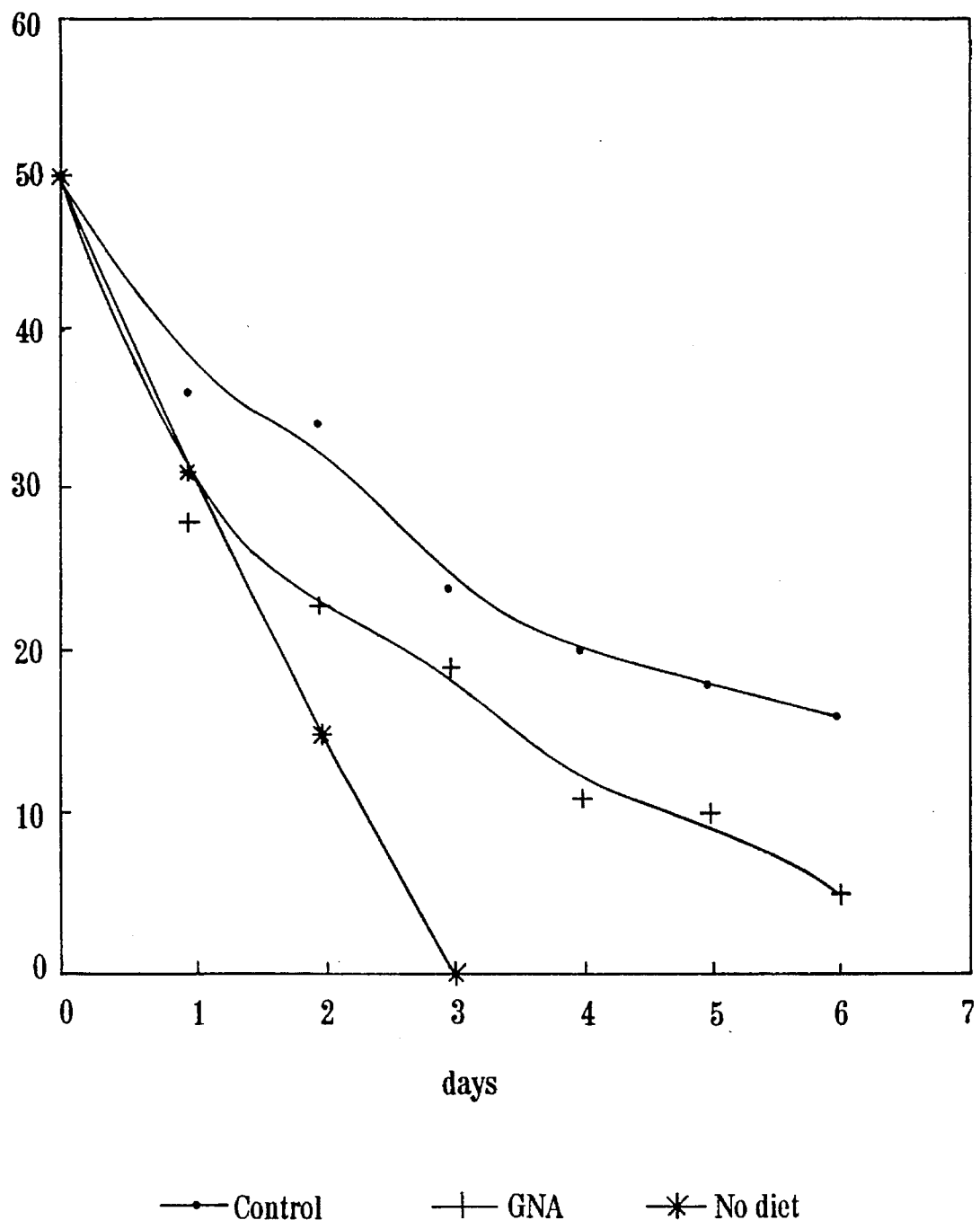

Aphids were maintained in the laboratory on tobacco plants [*Nicotiana tabacum* var. Samsun NN]. Artificial diet bioassays with GNA were carried out as described above, using the hydrostatic pressure assay system described in 1.3, against neonate, alate nymphs on an unmodified version of the diet described by Mittler and Dadd [1962: *Nature* 195, 404]. The results [FIG. 2] demonstrate that GNA substantially reduces survival of the green peach aphid on artificial diets. Although the corrected mortality, according to the procedures described in section 1.3, is less than that for the other Homopterans tested [25±4%], the protein clearly has significant deleterious effects on insect survival. It also has deleterious effects on development of the surviving insects—the size of live insects was measured by image analysis after 4 days on the diet: the results [Table 5] show a significant reduction in the mean size of nymphs on the diet containing GNA. Such a reduction in size of the nymphs is expected to have serious effects on the development time and fecundity of the insects and hence to significantly reduce the rate of aphid population growth.

TABLE 5

Size of aphids recovered from control and GNA containing artificial diets.

| | CONTROL | +GNA | F | $p_{[HO:m1=m2]}$ |
|---|---|---|---|---|
| MEAN LENGTH [mm ± SEM] | 0.86 ± .03 | 0.61 ± .01 | 62.809 | <0.01 |
| MEAN WIDTH [mm ± SEM] | 0.38 ± .02 | 0.26 ± .01 | 41.795 | <0.01 |

Thus, certain proteins, including but not restricted to GNA, may be identified which are effective against a wide range of Homopteran insect types.

EXAMPLE 2

Production of tissue specific promoter 2.1. 4×B2+A

The CaMV35S gene promoter is known to those skilled in the art as a strong constitutive promoter which is active in most organs of transgenic plants. Its overall activity is governed by the interaction of a number of distinct domains and sub-domains, various combinations of which have been studied and shown to confer different patterns of expression in transgenic plants [Fang et al. {1989} *The Plant Cell* 1, 141–150; Benfey et al. {1989} *EMBO J.* 8, 2195–2202; Benfey et al. {1990a} *EMBO J.* 9, 1677–1684; Benfey et al. {1990b} *EMBO J.* 9, 1685–1696]. The combination referred to as 4×B2+A has been shown to confer strong expression in vascular tissue, including phloem [Benfey et al., 1990a]. This combination comprises a four fold tandem repeat of region −155 to −102 of the 35S gene fused to the −90 to +8 region of the 35S gene [Benfey et al., 1990b] which would be particularly useful for the purposes of this invention.

The plasmid DNA designated pDB2, comprising the 4×B2 fragment inserted between the SalI and XhoI sites of plasmid pEMBL12x [pEMBL12x is a derivative of pEMBL12 with a XhoI site introduced 5′- of the BamHI site: the pEMBL family of phagemids are described in Dente et al. {1983} *Nucl. Acids Res.* 11, 1645–1655], and that designated pDA, comprising the A fragment inserted between the XhoI and SalI sites of pEMBL18, was obtained from Dr P. N. Benfey and [Laboratory of Plant Molecular Biology, Rockefeller University, N.Y.].

Figure 3A:
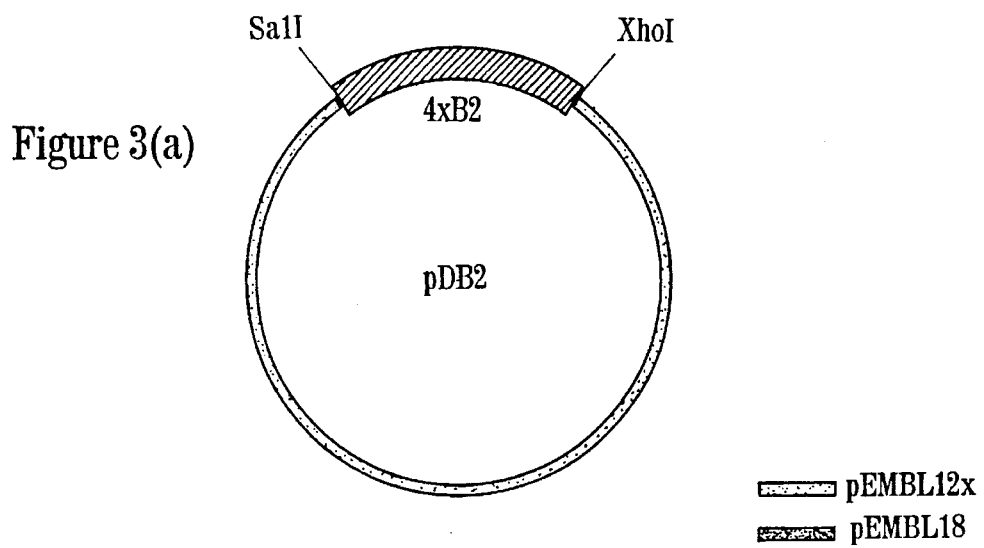
Figure 3B:
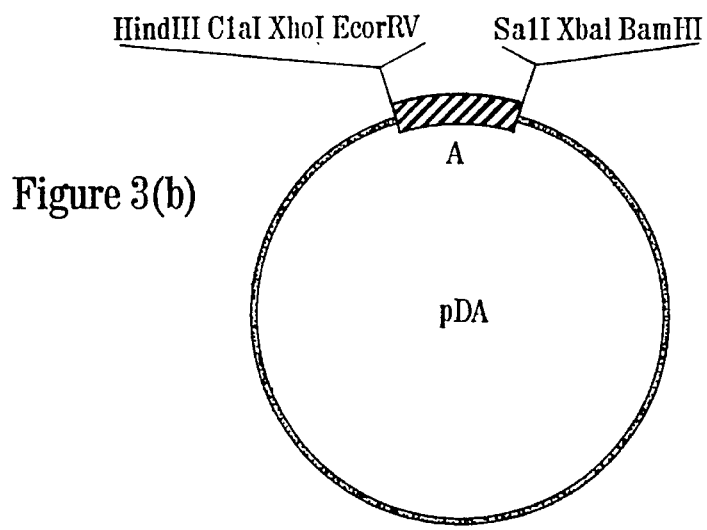
Figure 3C:
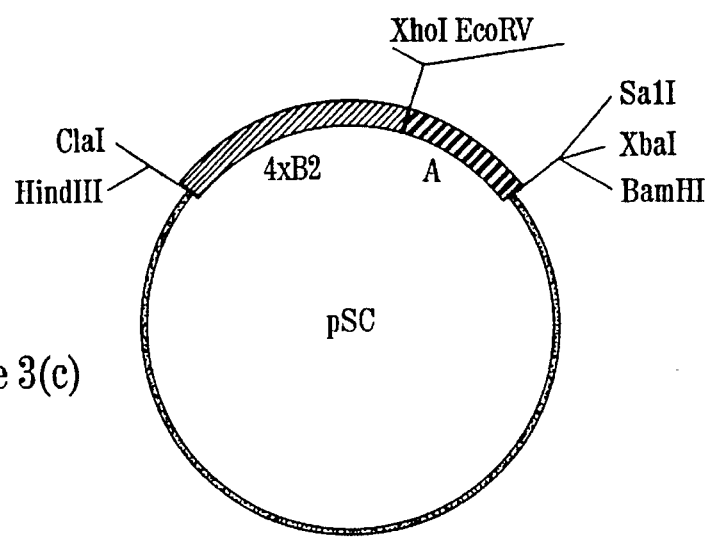

Plasmid DNAs were used to transform competent cells of *E. coli* DH5α [Northumbria Biologicals Ltd, Cramlington, U.K.] to ampicillin resistance. Plasmid DNA in this and subsequent examples was prepared by standard 'miniprep.' methods. DNA from pDB2 was digested with restriction enzymes SalI and XhoI and the restriction fragments separated by electrophoresis through an agarose gel. The 194 bp 4×B2 fragment was isolated from the gel and purified. This fragment was ligated with DNA from pDA which had been linearised by digestion with XhoI. This was used to transform competent *E. coli* DH5α to ampicillin resistance, yielding the clone containing the plasmid designated pSC, which contains the useful 4×B2+A promoter construct [FIG. 3].

2.2. Rice sucrose synthase

It might be considered particularly useful to express Homopteran-killing proteins in transgenic plants from an homologous promoter. Accordingly, this example provides an homologous promoter which gives effective expression in one of the most preferred plants, the monocotyledonous *Oryza satira*—rice, as well as being a useful phloem specific promoter for expression in heterologous systems.

The maize sucrose synthase 1 gene [Sh-1], encoding UDP-glucose: D-fructose 2-α-D-glucosyl transferase [EC 2.4.1.13] is one of the few monocotyledonous genes whose promoter sequence has been cloned [Burr, B. and Burr, F. {1982} *Cell* 29, 977–986; Geiser et al. {1982} EMBO J. 1, 1455–1460]. It has been demonstrated that the Sh-1 promoter, including the translation start site and the first intron in the 5'- untranslated region of the Sh-1 primary transcript, directs very, highly specific expression of foreign genes in the phloem cells of transgenic plants [Yang, N-S. and Russell, D. {1990} *Proc. natl. Acad. Sci.* USA 87, 4144–4148]. Maize Sh-1 gene sequences have been used to obtain the rice sucrose synthase promoter sequences as described below.

Synthetic oligonucleotides were produced by standard techniques. These sequences:

5'-TTCGTGCTGAAGGACAAGA (SEQ ID NO:1)

5'-CTGCACGAATGCGCCCTT (SEQ ID NO:2)

correspond to nucleotides +4264 to +4282 of the coding strand and +4564 to +4581 of the anti-coding strand of the published Sh-1 gene sequence [Werr, W. et al. {1985} EMBO J. 4, 1373–1380]. They were used as primers in the amplification of the Sh-1 gene fragment +4264 to +4581 from maize seedling genomic DNA using standard polymerase chain reaction [PCR] methods [eg. Innis, M. A. et al. eds. {1990} *PCR protocols: A Guide to Methods and Applications*. Academic Press, San Diego.]. The amplified product was cloned into the SmaI site of pUC18 according to standard techniques. This plasmid was designated pUEX. Plasmid pUEX is useful as a probe to identify rice sucrose synthase gene clones in rice genomic DNA libraries. Such libraries may be prepared or obtained by various methods known to those skilled in the art. In this example a commercially available rice genomic DNA library, in bacteriophage EMBL-3 was purchased from Clontech Laboratories Inc. [Palo Alto, USA]. Screening of 6.8×10$^5$ plaques by conventional methods with $^{32}$P-labelled insert from pUEX yielded 10 positive clones. Clone λRSS2.4 has been characterised as containing a full-length rice sucrose synthase 1 gene. This clone has been investigated in detail by restriction mapping, subcloning and sequencing by conventional methods [Wang, M. et al. {1992} *Plant Mol Biol.* 19, 881–885].

Figure 4:
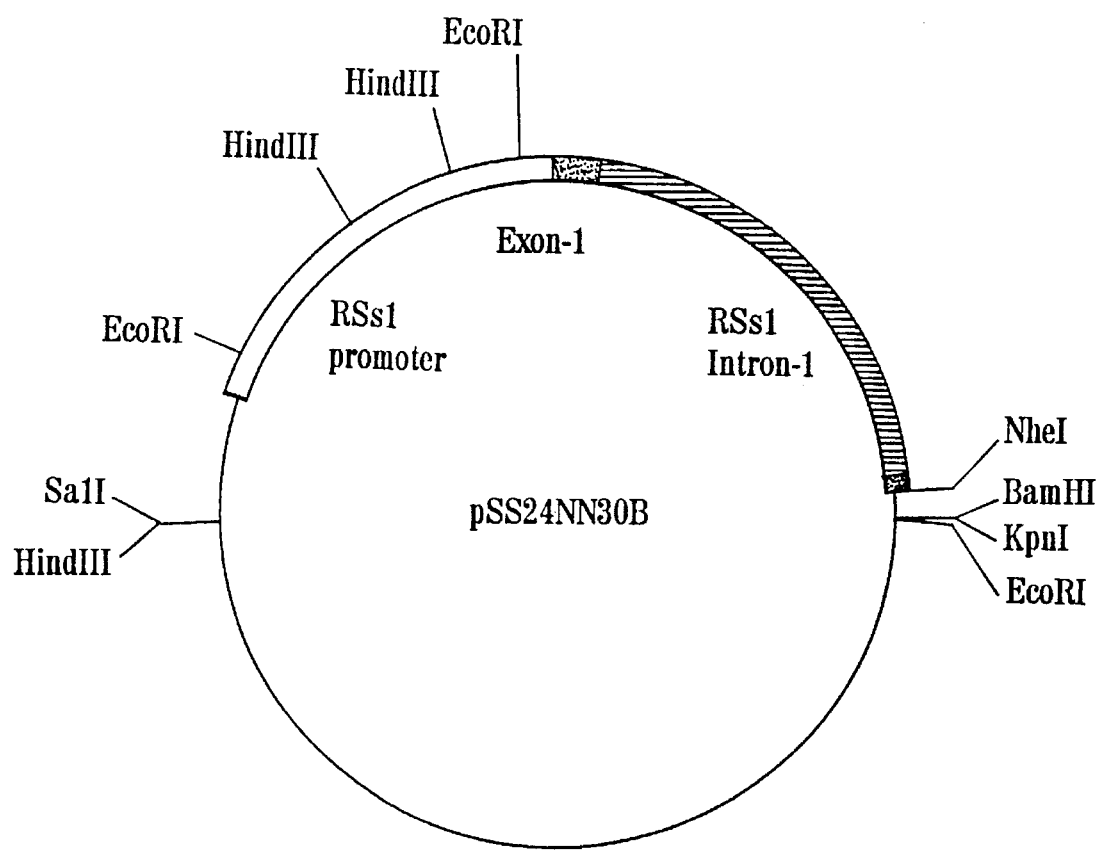

The rice sucrose synthase promoter/intron 1 sequence within λRSS2.4 has been identified by comparison with the Sh-1 sequence; it is located on a ca. 3.1 kb NheI restriction enzyme digest fragment. This fragment has been isolated and cloned into the XbaI site of plasmid pUC19 by standard techniques to yield plasmid pSS24NN30B—a useful intermediate plasmid containing the RSs1 promoter/intron 1 sequences [FIG. 4]. The part of the sequence of this 3.1 kb fragment which is useful for the purposes of this invention is presented in FIG. 5: there is an additional 200 bp upstream of the illustrated sequence which is not required for the purposes of this invention and which could be wholly or partially removed by techniques such as restriction enzyme digestion, exonuclease digestion or PCR amplification which are well known in the art.

EXAMPLE 3

Plant expression constructs

One of the preferred proteins for the purposes of this invention is the snowdrop lectin and the following examples provide intermediate vectors for the expression of this protein in the phloem of transgenic monocotyledonous and dicotyledonous plants. Those skilled in the art will know that the methods can be easily adapted for other proteins. Similarly, although most of these examples employ some of the preferred promoters they may be easily adapted for other phloem specific promoters.

3.1. For expression of GNA in dicot phloem 3.1.1. From the 4×B2+A promoter

Figure 6A:
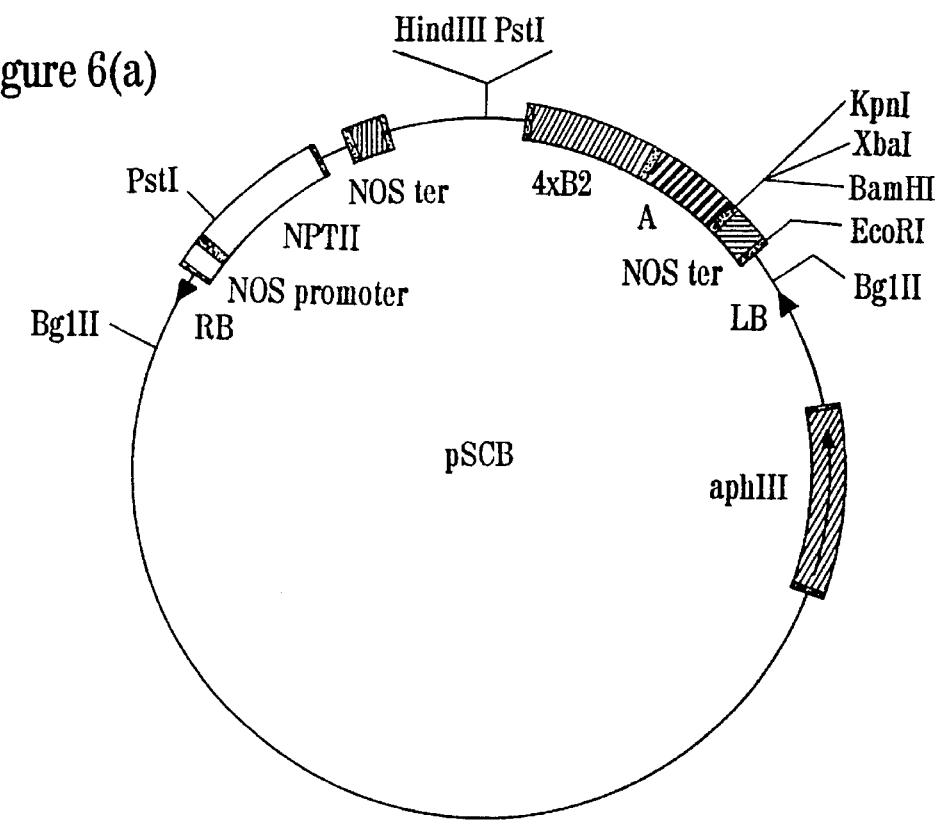
Figure 6B:
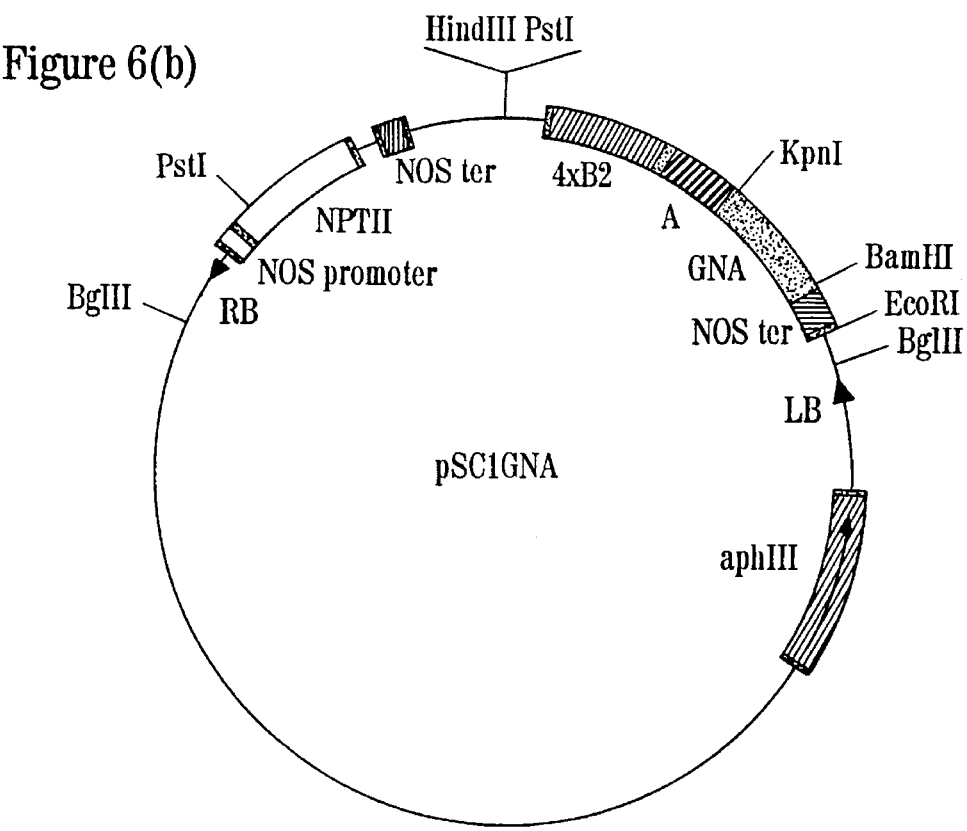

The Agrobacterium binary vector pROK2 [Hilder et al. {1987} *Nature* 330, 160–163] was digested with restriction enzymes HindIII and BamHI to excise the CaMV35S gene promoter. Plasmid pSC [example 2.1. above] was digested with HindIII and BamHI and the 292bp fragment containing the 4×B2+A sequence purified from agarose gel electrophoretic separation of the restriction fragments. This fragment is ligated to the HindIII/BamHI cut pROK fragment to yield pSCB [FIG. 6], a cassette for plant expression from the 4×B2+A promoter.

Plasmid p1GNA2, which is fully described in International Patent Application No. PCT/GB91/01290 [Agricultural Genetics Co.] was provided by Dr W. D. O. Hamilton [A.G.C.-A.P.T.L., Babraham, U.K.]. This contains the entire coding sequence for a GNA precursor protein between the BamHI and KpnI sites of pUC19. The GNA sequence was isolated by digestion of p1GNA2 DNA with BamHI and KpnI and extraction of the 490 bp fragment from agarose gel electrophoretic separation of the restriction fragments. This fragment was ligated into pSCB which had been digested with BamHI and KpnI to yield the plasmid designated pSC1GNA [FIG. 6] a vector suitable for the expression of GNA from the 4×B2+A promoter in transgenic plant phloem.

3.1.2. From the RSs1 promoter

Plasmid pBI101.2 is a commercially available [Clontech Laboratories Inc., Palo Alto, Calif.] *A. tumefaciens* binary vector derived from pBIN19 which contains a promoterless GUS gene cassette. Plasmid DNA was digested with restriction endonucleases SalI and BamHI and ligated with the SalI- BamHI restriction fragment isolated from digests of plasmid pSS24NN30B [example 2.2] to yield plasmid pBRSS7—a binary vector suitable for the expression of GUS from the RSs1 promoter in transgenic plants. This construct has been introduced into transgenic tobacco by standard Agrobacterium mediated gene transfer and the phloem specificity of expression from this promoter in dicotyledenous transgenics has been demonstrated by standard cytological GUS assays.

Figure 7:
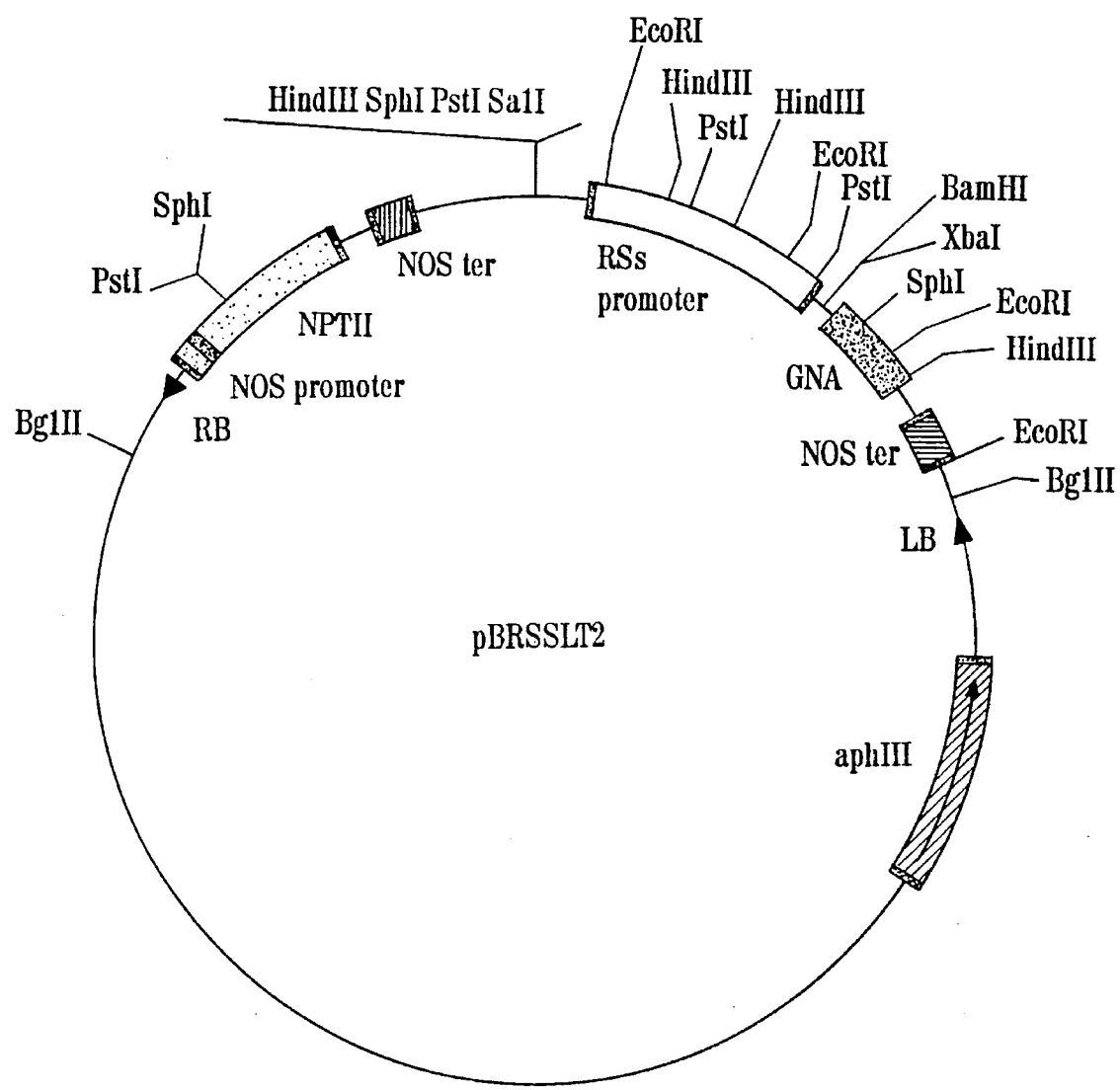

The GUS gene has been removed from plasmid pBRSS7 by digestion with restriction endonucleases SmaI and SstI and the 3'- overhang removed from the SstI site by treatment with T4 DNA polymerase. The GNA encoding sequence was prepared from plasmid p1GNA2 as a SmaI - PstI restriction fragment, and the 3'- overhang of the PstI site removed by treatment with T4 polymerase. These fragments were blunt-end ligated together and cloned into *E. coli* DH5α. Clones containing the GNA encoding sequence in the functionally correct orientation with respect to the RSs1 promoter were identified by diagnostic restriction analysis using HindIII [which produces a ca 2.1 kb fragment containing the GNA sequences in the correct orientation cf. ca 1.5 kb in the reverse orientation] and EcoRI [which produces a ca 1.7 kb fragment containing the GNA sequences in the correct orientation cf. <0.6 kb] yielding the plasmid designated pBRSSLT2 [FIG. 7] a binary vector suitable for the expression of GNA from the RSs1 gene promoter in transgenic plant phloem.

It will be noted that this construct contains an in-frame translation initiation codon, derived from exon2 of RSs1, 36 nucleotides upstream of the GNA preprotein initiation codon. This results in an additional 12 residues at the amino-terminus of the GNA preprotein [3 derived from RSs1, 9 from the polylinker] as shown below:

ATGGGATCCCCGGGGGATCCTCTAGAGTCCGGTTCCATG (SEQ ID NO: 3)
M  G  S  P  G  D  P  L  E  S  G  S  M

This N-terminal extension is not considered important for the purposes of this invention.

3.2. For expression of GNA in rice phloem 3.2.1. From 4×B2+A promoter

Figure 8A:
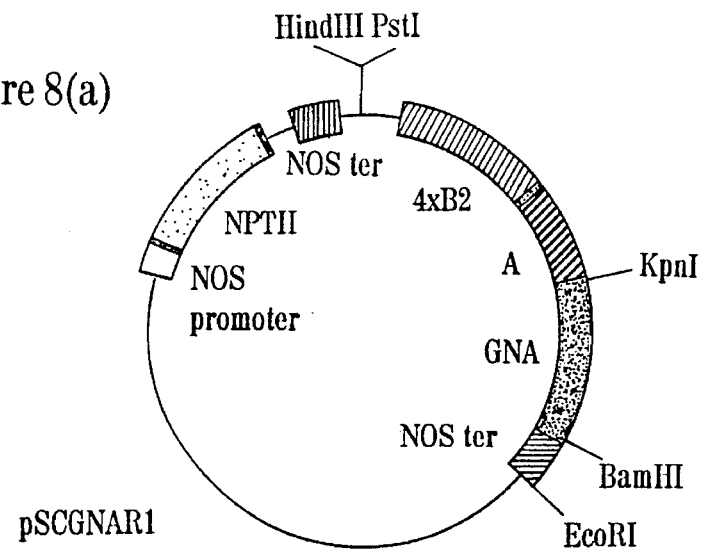
Figure 8B:
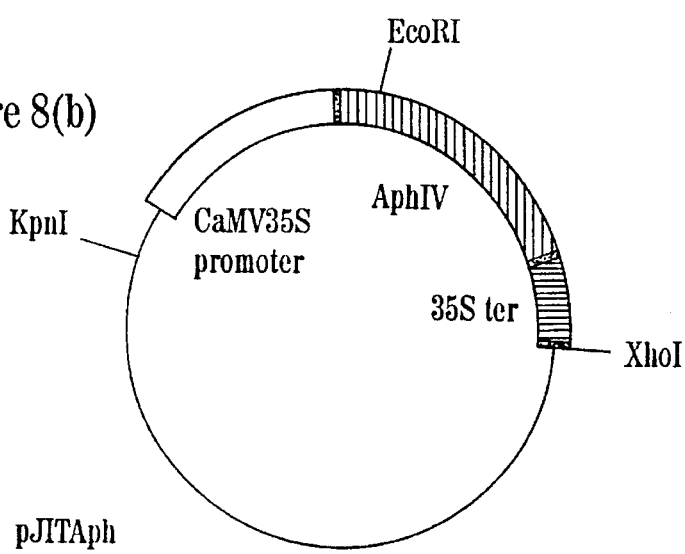
Figure 8C:
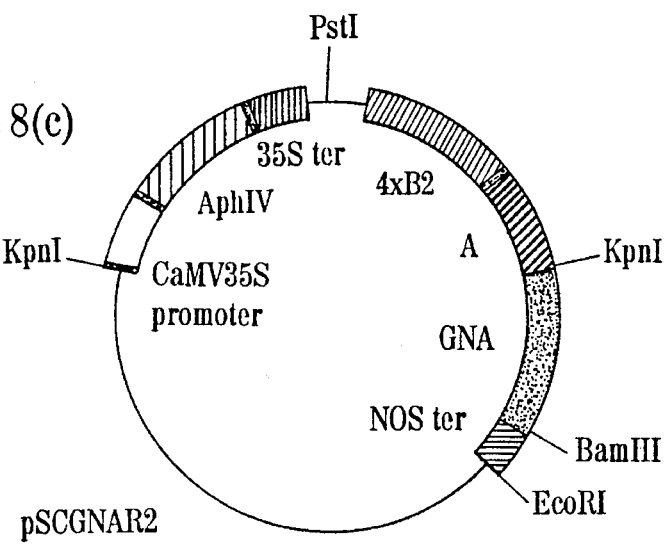

Plasmid pSC1GNA [example 3.1.1 above] was digested with BglII and EcoRI and the fragment containing the nptII gene and GNA expression construct was purified from agarose gel and ligated with BamHI and EcoRI digested pUC18. The resulting plasmid, designated pSCGNAR1 is useful for rice transformation [FIG. 8].

The nptII gene from transposon Tn5 has been used in all the preceding examples to allow selection of transformed plant tissue on kanamycin. It has, however, been claimed that kanamycin may cause sterility in transgenic rice [Li, Z. et al. {1990} *Plant Mol. Biol. Rep.* 8, 276–291]. The aphIV gene from *E. coli* was, therefore used to produce another construct for rice transformation, allowing selection of transformed plant tissue on hygromycin. Plasmid pJIT72 was digested with BamHI and HindIII and the 1110 bp fragment containing the aphIV gene sequence purified from agarose gel. Plasmid pJIT30Neo was digested with HindIII and EcoRI and the large fragment purified from agarose gel. The fragments were mixed and rendered blunt-ended by treatment with S1 nuclease. The nuclease was inactivated and the fragments ligated and used to transform competent cells of *E. coli* DH5α. Recombinant plasmids were screened by restriction analysis using KpnI+EcoRI and XhoI+EcoRI to identify a construct with the aphIV gene in the correct orientation relative to the promoter and terminator sequences. This construct was designated pJIT30Aph [FIG. 8]. Plasmid pSCGNAR1 was digested with HindIII and EcoRI and the GNA expression fragment purified from agarose gel. This fragment was mixed with pJIT30Aph which had been linearised by digestion with XhoI and the fragments rendered blunt-ended by treatment with S1 nuclease. The nuclease was inactivated and the fragments ligated and used to transform *E. coli* DH5α. The resultant construct, designated pSCGNAR2 [FIG. 8] is useful for expression of GNA in the phloem of transgenic rice plants which are resistant to hygromycin. The intact pSCGNAR2 or PstI linearised plasmid may be used for rice transformation.

3.2.2. From RSs1 promoter

Figure 9:
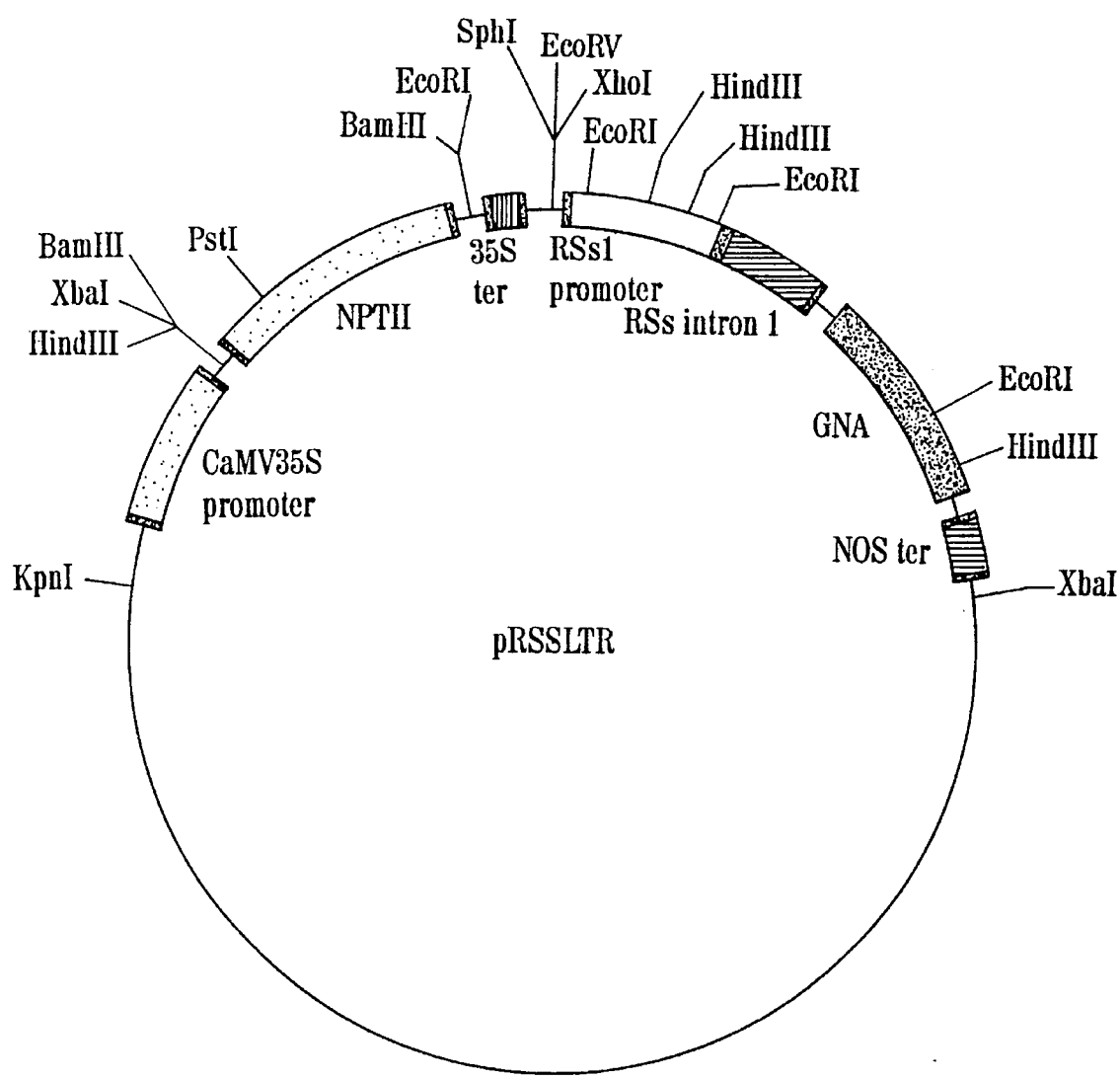

The << rice sucrose synthase promoter—GNA encoding sequence—nopaline synthase terminator -Ti plasmid left border >> DNA fragment from plasmid pBRSSLT2 [example 3.1.2 above] was isolated from a restriction endonuclease SalI/BglII digest. This fragment was cloned between the SalI and BamHI sites of the commercially available vector plasmid pSK [Stratagene, San Diego, Calif.] to yield plasmid pKRSSLT. These sequences were subsequently isolated from pKRSSLT on a KpnI/XhoI restriction endonuclease digestion fragment and cloned between the KpnI and XhoI sites of pJIT30 to yield plasmid pRSSLTR [FIG. 9], which is useful for expression of GNA from the RSs1 promoter in the phloem of transgenic rice plants.

EXAMPLE 4

Production of transgenic plants 4.1. Transgenic tobacco

The GNA expression constructs pSC1GNA [example 3.1.1] and pBRSSLT2 [example 3.1.2] have been mobilised into *Agrobacterium tumefaciens* LBA4404 by triparental mating with *E. coli* HB101 harbouring pRK2013 by standard procedures [Bevan, M. {1984} *Nucl. Acids Res.* 12, 103–110]. The GNA gene construct was then introduced into tobacco plants [*Nicotiana tabacum* var. Samsun NN] by Agobacterium mediated gene transfer using leaf discs, and mature transgenic tobacco plants regenerated according to established protocols [Fraley et al. {1983} *Proc. Natl. Acad. Sci.* USA 80, 4803–4807; Horsch et al. {1985} *Science* 227, 1229–1231]. Expression levels of GNA may be determined immunologically using rabbit anti-GNA antiserum and $^{35}$S-labelled donkey anti-rabbit IgG [Amersham International plc, Amersham, U.K.] secondary antibody on protein extract dot-blots according to established methods [Jahn et al. {1984} *Proc. Natl. Acad. Sci. USA* 81, 1684–1687]. Imprints of cut stem and leaf sections on nitrocellulose membranes have been probed with the anti-GNA primary antibody and visualised using an enhanced chemiluminescence [ECL] system using HRP-conjugated goat anti-rabbit secondary antibody [Bio-Rad Laboratories Ltd., Warford, U.K.] and commercially available ECL immunoassay signal detection reagents [Amersham International plc., Amersham, U.K.]. This has demonstrated phloem specific expression of GNA from these promoters. Selected plants have been allowed to self-set seed and individuals in the S1 generation which are homozygous for the inserted genes may be identified by segregation analysis of kanamycin resistance in the S2 generation. Homozygous, GNA-expressing S2 plants are bioassayed for resistance to pest Homopterans by infesting whole plants with peach-potato aphids [*Myzus persicae*].

The CaMV35S gene promoter is known in the art as a strong, constitutive promoter which is active in most tissues of transgenic plants, including the vascular tissues. The introduction into transgenic tobacco plants of gene constructs which lead to expression of GNA from the CaMV35S gene promoter, for a purpose different to the present invention, has been detailed in International Patent Application No. PCT/GB91/01290 [Agricultural Genetics Co.]. Clonal replicates of transgenic *N. tabacum* var. Samsun NN plants [produced from stem cuttings by standard techniques] derived from one of these GNA-expressing lines, designated 15GNA1#79, and of non-expressing control plants, were obtained from Agricultural Genetics Company APTL, Babraham, Cambridge. The location and relative levels of expression of GNA in this line has been determined by immunocytological investigation of thin sections through leaf and stem material, using polyclonal rabbit anti-GNA primary antibody and HRP-conjugated secondary antibody.

It has now been shown that the apparent level of expression of GNA in the phloem of 15GNA1#79 tobacco plants, relative to the mesophyll, is higher than would be expected from our own and published observations on relative levels of GUS gene expression directed by the CaMV35S gene promoter in transgenic tobacco plants. The difference in the relative levels of expression of the two genes may be a result of differences in the intracellular targetting of the genes.

Because of the relatively high level of expression of GNA in the phloem of 15GNA1#79 plants from a non-optimal promoter, it was considered useful to test these plants in bioassays against the peach potato aphid.

4.2. Transgenic rice

The GNA gene expression constructs may be introduced into rice plants [*O. sativa*] by any of a number of established protocols known to those skilled in the art [Shimamoto et al. {1989} *Nature* 338, 274–276; Yang et al. {1988} *Plant Cell Rep.* 7, 421–425; Zhang et al. {1988} *Plant Cell Rep.* 7, 379–384; Li et al. {1990} *Plant Mol. Biol. Rep.* 8, 276–291]. This example uses the procedures of Yang et al. [1988] to provide transgenic rice plants which express GNA in phloem.

The 'Taipei 309' variety of rice, obtained from IRRI, is used as a source of cell suspension cultures from which protoplasts may be prepared by enzymatic digestion of the cell wall with cellulase and pectinase. Protoplasts are incubated with pSCGNAR1 or pSCGNAR2 [example 3.2.1] or with pRSSLTR [example 3.2.2] and treated with an electrical pulse to induce uptake of the plasmid DNA. Protoplasts are cultured on a medium containing the antibiotics kanamycin [pSCGNAR1 and pRSSLTR] or hygromycin [pSCGNAR2] to select for transformed cells. Antibiotic resistant calli are transferred to regeneration medium to produce transgenic rice plantlets which are subsequently grown to maturity in soil. The regenerants may be analysed for expression of GNA by immunological methods as in Example 4.1. Homozygous transgenic plants are obtained by self-pollination as described for tobacco in example 4.1 and used to bioassay for resistance to the sap-sucking pest insect—in this case the brown planthopper, using non-transformed 'Taipei 309' plants as controls. Seed is collected from those plants showing the desired resistance characteristics and plants derived from these lines may be propagated and incorporated into conventional rice improvement programmes.

EXAMPLE 5

Sap-sucking insect bioassays of transgenic plants

Transgenic tobacco plants which express GNA in their phloem [example 4.1] have been tested in bioassays against *Myzus persicae*—the peach potato aphid—which was maintained as described in example 1.5.

5.1. Whole plant bioassays

Figure 10:
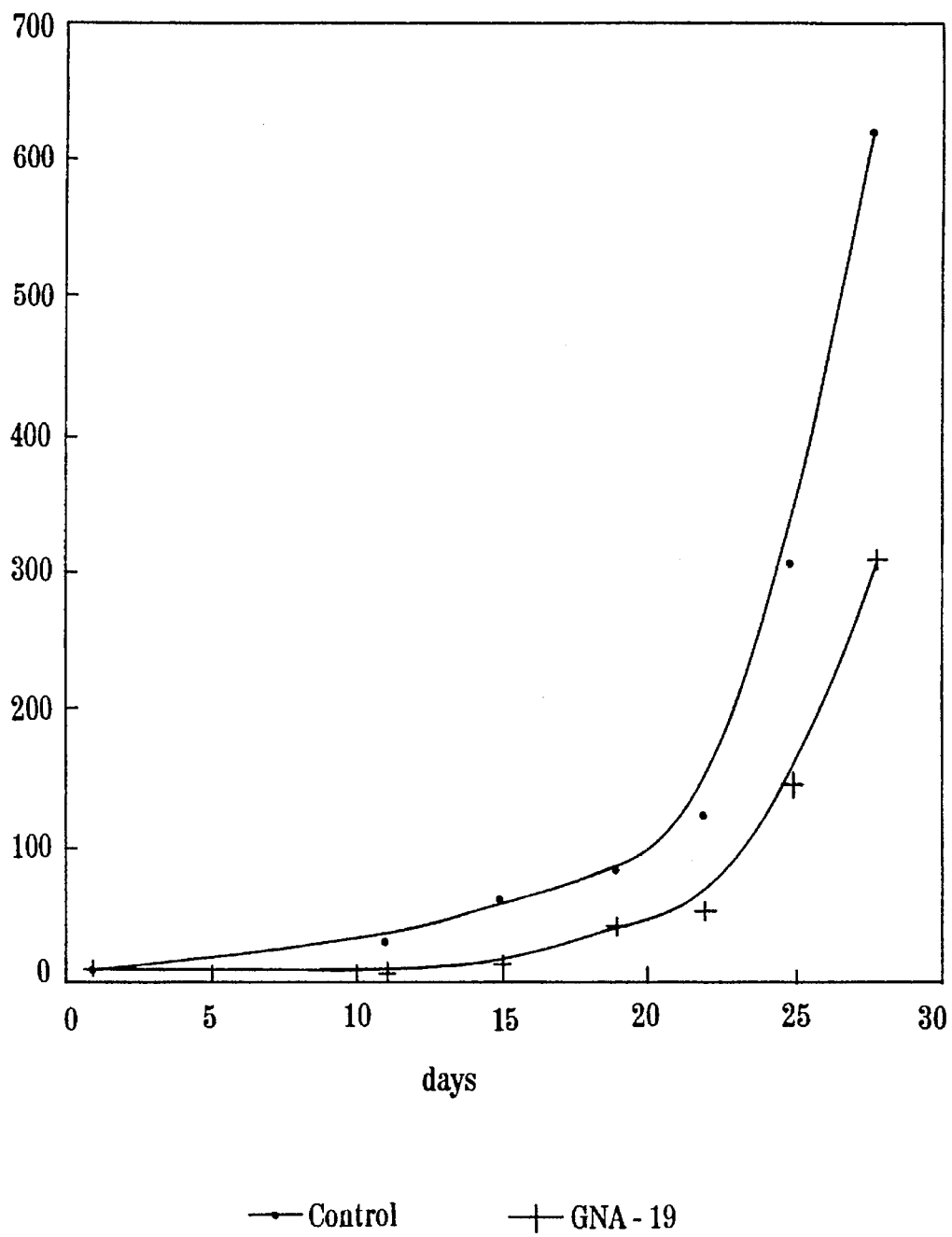

Clonal replicates of transgenic tobacco line 15GNA1#79 [example 4.1] were produced from stem cuttings by standard techniques. These plants, and clonally propogated, untransformed *N. tabacum* var. Samsun control plants were potted into 5 inch pots and grown in individual 24×24×40 cm perspex boxes within a controlled environment growth room. When ca. 20 cm tall, the plants were infested with 8 late instar, alate aphids. Growth of the aphid population was monitored by counting all aphids on each plant. The results, illustrated in FIG. 10, demonstrate a significant reduction in the size of the aphid population on the transgenic plants. The rate of growth of the aphid population may be estimated from the doubling time, $T^D$, where $$T^D = 0.30103/m$$

'm' being the slope of the regression of $\log_{10}$ aphid numbers on time. $T^D$ is increased on the transgenic plants to 4.8±0.2 days compared with 4.4±0.2 days on the controls.

5.2. Leaf disc bioassays

Control and GNA-expressing transgenic plants were grown to 30–40 cm high. Discs of 25 mm diameter were cut from fully mature leaves, avoiding areas of leaf with large veins. Leaf discs were floated upside-down on 10 ml tap water in 5cm diameter disposable petri dishes. Two late instar, alate aphid nymphs were applied to each leaf disc and the dishes, lidded were maintained in the controlled environment growth chamber. Aphids were counted daily.

Figure 11:
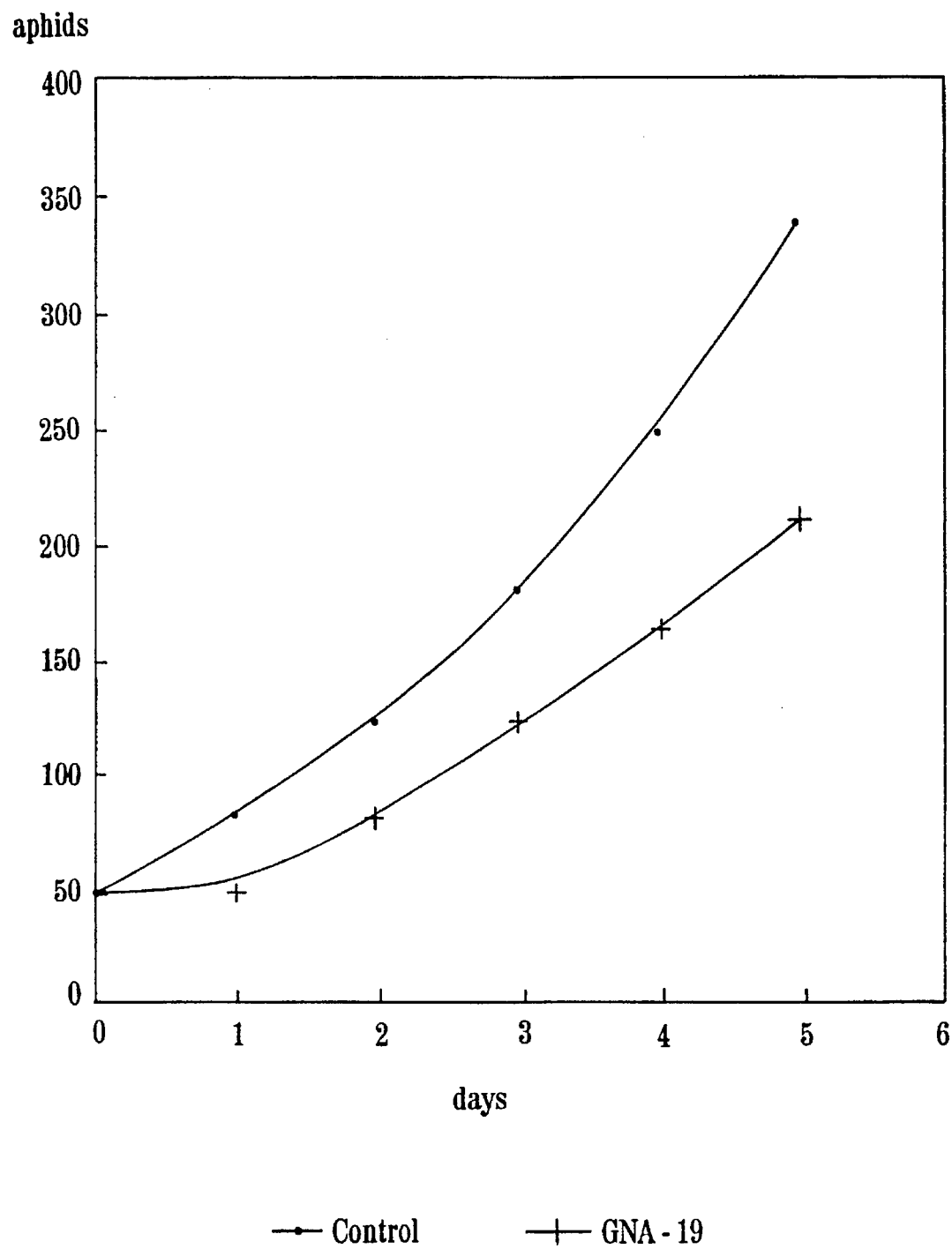

The results, illustrated in FIG. 11, demonstrate a significant reduction in the size of the aphid population on the transgenic plants. Thus the results obtained from the leaf disc bioassay mirror those obtained in whole plant bioassays; the former has the advantage of allowing a greater number of replicates to be carried out.

The aphid population doubling time, calculated as above, is greater on the leaf discs produced from transgenic plants $[T^D=2.47$ days] than on the controls $[T^D=1.62$ days].

Leaf disc bioassays were repeated using leaves from a number of individual replicate control and transgenic plants and replicates from a number of different leaves within an individual control and transgenic plant. Statistical analysis of the number of aphids per leaf disc after 7 days bioassay show a clearly significant reduction in number of aphids on the discs taken from transgenic plant leaves [Table 6]. Coefficients of variation for leaves within the same plant were about 20%; the coefficient of variation for different replicate control plants was 54%, for different replicate transgenic plants 75%.

TABLE 6

| Leaf disc bioassay of different replicated GNA-expressing transgenic and control tobacco plants against *M. persicae*. | | | |
|---|---|---|---|
| | MEAN APHIDS/DISC | N | SEM |
| CONTROL | 38.8 | 6 | ±8.6 |
| 15GNA1#79 | 8.3 | 6 | ±2.5 |

In order to establish whether those aphids which survive on the GNA expressing transgenic plants represent an inherently resistant subgroup, leaf disc bioassays were performed comparing the performance of aphids which had been maintained on control tobacco plants with those which had been maintained on GNA-expressing transgenic tobacco plants for six weeks, during which time the aphids should have gone through several generations. The results [Table 7] show that GNA-conditioned aphids are equally susceptible to the effects of GNA expression in transgenic tobacco plants.

TABLE 7

Leaf disc bioassay of control and GNA-expressing transgenic tobacco plants against *M. persicae* conditioned on control or GNA-expressing transgenic tobacco plants.

| SOURCE OF LEAF DISC | MEAN APHIDS/DISC [±SEM] SOURCE OF APHIDS | |
| --- | --- | --- |
|  | CONTROL | GNA |
| CONTROL | 11.8 ± 3.0 | 12.0 ± 2.8 |
| 15GNA1#79 | 3.3 ± 1.8 | 2.5 ± 1.8 |

These bioassays demonstrate that proteins identified as being effective against Homopterans in artificial diets are also effective against these insects when expressed in the phloem of transgenic plants.

We claim:

1. A method of controlling Homopteran insect pests, which comprises administering enterally to the pests a protein which has toxic or antimetabolic effects on them, the protein being expressed in the phloem of a transgenic plant comprising a gene coding for the protein, the gene being associated with a phloem specific promoter which causes the gene to express the protein in the phloem of the plant.

2. A method according to claim 1, wherein the protein is selected from the group consisting of lectins and lipoxidases.

3. A method according to claim 2, wherein the lectin is snowdrop lectin or wheatgerm agglutinin, and the lipoxidase is pea lipoxidase 1 or soybean lipoxidase.

4. A method according to 1, wherein the promoter is selected from the group consisting of the 4×B2+A promoter, the rice sucrose synthetase gene promoter and the oilseed rape extensin gene promoter.

5. A method according to claim 1, wherein the plant is a transformable plant.

6. A method according to claim 1, wherein the transformable plant is selected from the group consisting of rice and maize.

7. A method according to claim 1, wherein the Homopteran insect pests are selected from the group consisting of aphids, planthoppers, leafhoppers, whiteflies, froghoppers and scales.

8. A method according to claim 1, in which the protein is one which, when added to a feeding diet for the insect pests, gives an increase in mortality of at least 50% compared with the diet not including the protein.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TTCGTGCTGA AGGACAAGA    19

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

CTGCACGAAT GCGCCCTT    18

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | |
|---|---|---|---|
| ATGGGATCCC | CGGGGATCC | TCTAGAGTCC | GGTTCCATG | 39 |

(2) INFORMATION FOR SEQ ID NO:4:

(i) SEQUENCE CHARACTERISTICS:
        (A) LENGTH: 2914 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

| | | | | | |
|---|---|---|---|---|---|
| CTCCTTCATT | TTCAGTGCAA | ATGTGCAATG | CTGATTAGAG | TTTGCAGATG | CTGTTTGGTT | 60 |
| TAGTTTAGAT | GTGGCATTTT | GTTAGTGGTT | TCTTTGATGA | AAAATTCTTG | GCTATGATAA | 120 |
| AGTTTGCTTT | CTGAATATAT | GAATAGTGGC | CATGGTTCAA | GAAACTCCAG | TTAGGTGGGA | 180 |
| TAATTTATGG | TGATTCTGGG | CGCAATTCGG | GGAAATTTTT | TTTGGCGAGA | ATCTTATCAT | 240 |
| TGAGATAAAG | AGGGCAAGAA | TATCAACAGA | CTTTTAATCT | TAATAAAAAG | CACTCTTAGC | 300 |
| GTAAGAGCAA | AGCATTGCAA | TCTCGTGTGA | CAAGAACGTT | TCTTTTTCTC | CATCTTTTTC | 360 |
| TTTTTTACCA | AAAAATGAGT | GTTGCCAACT | GCTGCACCTT | CTTAGGCCGG | TTTGTTCTTG | 420 |
| TTTGGAACGC | ACGGAATGCC | CGATGCAAAA | AAAAAAAAGA | AATGCTGTTA | ACAAATCACT | 480 |
| GTCCTGACAC | GGCTAATTAG | GTGGTAATTT | GGTGCATCTG | CAAAGAAGCA | ACAGATGCTT | 540 |
| TCTTTCACTG | AAAGCATATT | TGCATGATTT | CTTGTTTCTG | CTTGTCCTCT | CTCTGATGCT | 600 |
| GACTGTATTC | CACTCTGCGC | TGTAATGCCA | TGTTAGTGAT | TAATATGTTC | AAAAGAGCAT | 660 |
| AAAAGAATTG | CCAATTGGAT | GTTAGAGATT | ACTGTGTTGT | TCAAAAGAGC | ATAAAAGAAT | 720 |
| TACCAATTTG | ATGGTAGATG | TTACTAGCAC | CACCTTGGTG | TTTCCCCATG | GTTTCTGCA | 780 |
| ATTCTGCCCA | TGATCTTTCT | GCTTTTCTGA | AAGACCTATG | TTTCAGAGGT | CAAGCTTCTG | 840 |
| GAAGGTTATT | AGGAGGGATG | AGTCGTCATT | TTGTCTGTGG | GCCCCACTAG | TCAGTGTCAA | 900 |
| TAGTTGTAAA | GGGTAGAAAT | TTTCTTGCTG | TTTTTCTTGG | AAACAATTTC | ATTGCGCCTG | 960 |
| ATCTGATGGT | CGGTCTGGTA | ATCAAATCAC | CAGATCCTGA | AATCCACCAA | ATCAAACCGT | 1020 |
| GAGATTTTTG | CAGAGGCAAA | ACAAGAAAAG | CATCTGCTTT | ATTTCTCTCT | TGCTTTCTTT | 1080 |
| TCATCCCCAA | CCAGTCCTTT | TTTCTTCTGT | TTATTTGTAG | AAGTCTACCA | CCTGCAGTCT | 1140 |
| ATTATTCTAC | AGAGAAAAAG | ATTGAAGCTT | TTTTTCTCCA | AAGCTGACAA | TGGTGCCGGC | 1200 |
| ATATGCTAAT | AGGATACTCC | CTTCGTCTAG | GAAAAAACCA | ACCCACTACA | ATTTTGAATA | 1260 |
| TATATTTATT | CAGATTTGTT | ATGCTTCCTA | CTCCTTCTCA | GGTATGGTGA | GATATTTCAT | 1320 |
| AGTATAATGA | ATTTGGACAT | ATATTTGTCC | AAATTCATCG | CATTATGAAA | TGTCTCGTTC | 1380 |
| GATCTATGTT | GTTATATTAT | AGACGGAGAT | AGTAGATTCG | GTTATTTTG | GACAGAGAAA | 1440 |
| GTACTCGCCT | GTGCTAGTGA | CATGATTAGT | GACACCATCA | GATTAAAAAA | ACATATGTTT | 1500 |
| TGATTAAAAA | AATGGGGAAT | TTGGGGGGAG | CAATAATTTG | GGGTTATCCA | TTGCTGTTTC | 1560 |
| ATCATGTCAG | CTGAAAGGCC | CTACCACTAA | ACCAATATCT | GTACTATTCT | ACCACCTATC | 1620 |
| AGAATTCAGA | GCACTGGGGT | TTTGCAACTA | TTTATTGGTC | CTTCTGGATC | TCGGAGAAAC | 1680 |
| CCTCCATTCG | TTTGCTCGTC | TCTGACCACC | ATTGGGTATG | TTGCTTCCAT | TGCCAAACTG | 1740 |
| TTCCCTTTTA | CCCATAGGCT | GATTGATCTT | GGCTGTGTGA | TTTTTTGCTT | GGGTTTTTGA | 1800 |
| GCTGATTCAG | CGGCGCTTGC | AGCCTCTTGA | TCGTGGTCTT | GGCTCGCCCA | TTTCTTGCGA | 1860 |

| | | | | | | |
|---|---|---|---|---|---|---|
| TTCTTTGGTG | GGTCGTCAGC | TGAATCTTGC | AGGAGTTTTT | GCTGACATGT | TCTTGGGTTT | 1920 |
| ACTGCTTTCG | GTAAATCTGA | ACCAAGAGGG | GGGTTTCTGC | TGCAGTTTAG | TGGGTTTACT | 1980 |
| ATGAGCGGAT | TCGGGGTTTC | GAGGAAAACC | GGCAAAAAAC | CTCAAATCCT | CGACCTTTAG | 2040 |
| TTTTGCTGCC | ACGTTGCTCC | GCCCCATTGC | AGAGTTCTTT | TTGCCCCCAA | ATTTTTTTTT | 2100 |
| ACTTGGTGCA | GTAAGAATCG | CGCCTCAGTG | ATTTCTCGA | CTCGTAGTCC | GTTGATACTG | 2160 |
| TGTCTTGCTT | ATCACTTGTT | CTGCTTAATC | TTTTTGCTT | CCTGAGGAAT | GTCTTGGTGC | 2220 |
| CTGTCGGTGG | ATGGCGAACC | AAAAATGAAG | GGTTTTTTT | TTTGAACTG | AGAAAAATCT | 2280 |
| TTGGGTTTTT | GGTTGGATTC | TTTCATGGAG | TCGCGACCTT | CCGTATTCTT | CTCTTTGATC | 2340 |
| TCCCCGCTTG | CGGATTCATA | ATATTCGGAA | CTTCATGTTG | GCTCTGCTTA | ATCTGTAGCC | 2400 |
| AAATCTTCAT | ATCTCCAGGG | ATCTTTCGCT | CTGTCCTATC | GGATTTAGGA | ATTAGGATCT | 2460 |
| AACTGGTGCT | AATACTAAAG | GGTAATTTGG | AACCATGCCA | TTATAATTTT | GCAAAGTTTG | 2520 |
| AGATATGCCA | TCGGTATCTC | AATGATACTT | ACTAAAACCC | AACAAATCCA | TTTGATAAAG | 2580 |
| CTGGTTCTTT | TATCCCTTTG | AAAACATTGT | CAGAGTATAT | TGGTTCAGGT | TGATTTATTT | 2640 |
| TGAATCAGTA | CTCGCACTCT | GCTTCGTAAA | CCATAGATGC | TTTCAGTTGT | GTAGATGAAA | 2700 |
| CAGCTGTTTT | TAGTTATGTT | TTGATCTTCC | AATGCTTTTG | TGTGATGTTA | TTAGTGTTGA | 2760 |
| TTTAGCATGG | CTTTCCTGTT | CAGAGATAGT | CTTGCAATGC | TTAGTGATGG | CTGTTGACTA | 2820 |
| ATTATTCTTG | TGCAAGTGAG | TGGTTTTGGT | ACGTGTTGCT | AAGTGTAACC | TTTCTTTGCA | 2880 |
| GTTCCTGAAA | TTGAGTCATG | GCTGCCAAGC | TAGC | | | 2914 |